(12) United States Patent
Boettger et al.

(10) Patent No.: US 8,546,343 B2
(45) Date of Patent: Oct. 1, 2013

(54) AMINOGLYCOSIDE ANTIBIOTICS TARGETING BACTERIAL 16S RIBOSOMAL RNA

(75) Inventors: Erik C. Boettger, Zürich (CH); Andrea Vasella, Zürich (CH); Deborah Perez Fernandez, Cambridge, MA (US)

(73) Assignees: Eidgenoessische Technische Hochschule Zurich, Zurich (CH); Uiniversitat Urich Prorektorat Forschung, Zurich (CH)

( * ) Notice: Subject to any disclaimer, the term of this patent is extended or adjusted under 35 U.S.C. 154(b) by 211 days.

(21) Appl. No.: 12/449,213

(22) PCT Filed: Jan. 31, 2008

(86) PCT No.: PCT/EP2008/000768
§ 371 (c)(1),
(2), (4) Date: Jan. 15, 2010

(87) PCT Pub. No.: WO2008/092690
PCT Pub. Date: Aug. 7, 2008

(65) Prior Publication Data
US 2010/0144662 A1   Jun. 10, 2010

(30) Foreign Application Priority Data
Feb. 2, 2007   (EP) .................................... 07002363

(51) Int. Cl.
*A61K 31/70* (2006.01)
*C07H 15/20* (2006.01)

(52) U.S. Cl.
USPC ............................................ 514/39; 536/13.3

(58) Field of Classification Search
None
See application file for complete search history.

(56) References Cited

U.S. PATENT DOCUMENTS
3,956,274 A * 5/1976 Umezawa et al. ........... 536/13.3

OTHER PUBLICATIONS

Draker et al. Biochemistry, 2003, 42, 6565-6574.*
Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Watanabe et al., Bulletin of the Chemical Society of Japan, vol. 48(8), pp. 2303-2305, 1975.*
Riguet, E., et al., "A route for preparing new neamine derivatives targeting HIV-1 TAR RNA", *Tetrahedron*, Elsevier Science Publishers; Amsterdam, NL, www.sciencedirect.com, vol. 60, No. 37, Sep. 6, 2004, pp. 8053-8064, XP004527590.
Kudyba, I., et al., "Synthesis of paromomycin derivatives modified at C(5") to selectively target bacterial rRNA", *Carbohydrate Research*, www.sciencedirect.com. 342, pp. 499-519, 2007, XP-002441570.

* cited by examiner

*Primary Examiner* — Traviss C McIntosh, III
(74) *Attorney, Agent, or Firm* — Nath, Goldberg & Meyer; Tanya E. Harkins

(57) ABSTRACT

The present invention relates to paromamine-based compounds according to formula I having selective antimicrobial activity directed at ribosomal 16S RNA. Furthermore, the invention is directed to the use of said compounds for preparing a medicament, pharmaceutical preparations and methods for preparing said compounds.

34 Claims, 2 Drawing Sheets

AMINOGLYCOSIDE ANTIBIOTICS TARGETING BACTERIAL 16S RIBOSOMAL RNA

Figure 1:
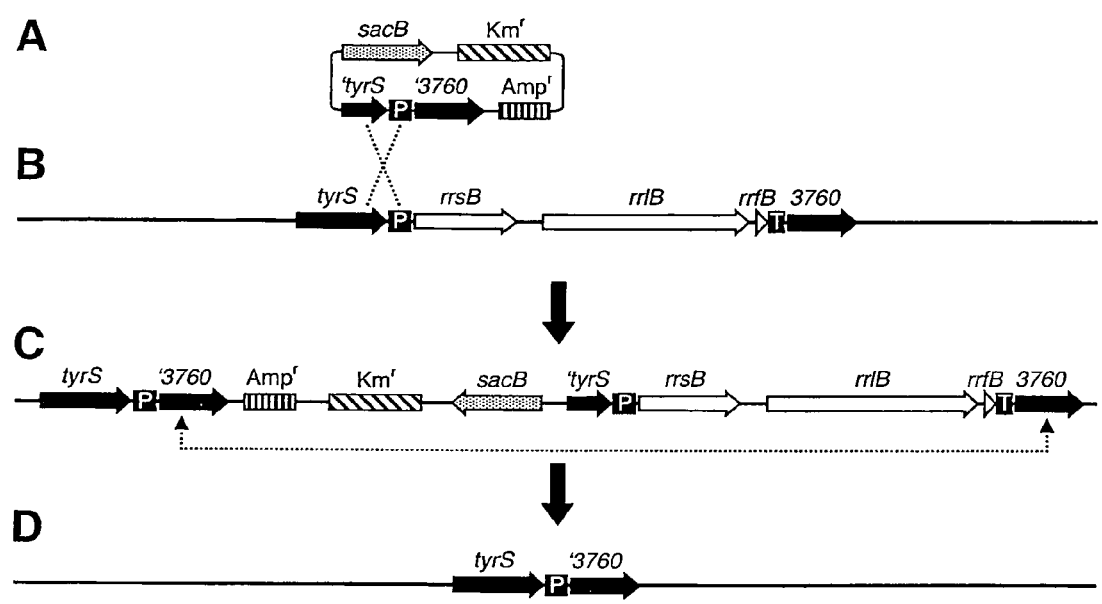

This is a National Phase Application filed under 35 U.S.C. 371 as a national stage of PCT/EP2008/000768, with the filing date of 31 Jan. 2008, an application claiming priority benefit from European patent Application No. 07002363.5, filed on 2 Feb. 2007, the entire content of each of which is hereby incorporated by reference in its entirety.

FIELD OF THE INVENTION

The present invention relates to paromamine-based compounds according to formula I having selective antimicrobial activity directed at ribosomal 16S RNA. Furthermore, the invention is directed to the use of said compounds for preparing a medicament, pharmaceutical preparations, and methods for preparing said compounds.

BACKGROUND OF THE INVENTION

Aminoglycoside antibiotics (AGAs) are clinically important drugs effective against a broad range of microorganisms. The clinical use of AGAs is restricted by toxicity (irreversible ototoxicity and reversible nephrotoxicity) and by the resistance of pathogens to AGAs. Common to 2-deoxystreptamine derived AGAs is a pseudodisaccharide core of the neamine type. It is composed of 2-deoxystreptamine (ring II) glycosidically linked to an aminodeoxyglucopyranose (ring I). Additional glycosyl moieties are attached to the hydroxy groups of the 2-deoxystreptamine moiety to give rise to a variety of compounds, categorized as 4,5- or 4,6-substituted deoxystreptamine-derived aminoglycosides, such as paromomycin (1a) and kanamycin A (1b).

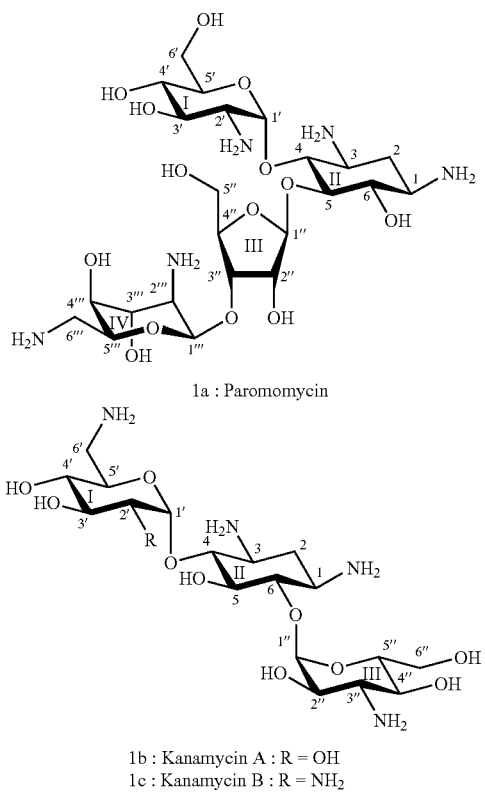

1a : Paromomycin

1b : Kanamycin A : R = OH
1c : Kanamycin B : R = NH$_2$

AGAs affect the fidelity of protein synthesis through binding to specific sites of the ribosomal RNA (rRNA) (Magnet et al., *Chem. Rev.* 2005, 105, 477; Jana et al., *Appl. Microbiol. Biotechnol.* 2006, 70, 140; Vicens et al., *Chembiochem* 2003, 4, 1018; Ogle et al., *Trends Biochem Sci* 2003, 28, 259). In spite of decades of use of ribosomal drugs, the structural features governing selectivity, i.e. the discrimination between prokaryotic and eukaryotic ribosomes, and the toxicity of these compounds are still not fully understood. Genetic studies (Hobble et al., *Antimicrob. Agents Chemother.* 2006, 50, 1489; Hobbie et al., C. *Antimicrob. Agents Chemother.* 2005, 49, 5112; Boettger et al., *EMBO reports* 2001, 2, 318) and crystal structures of AGAs complexed with ribosomal subunits (Carter et al. *Nature* 2000, 407, 340; Francois et al. *Nucleic Acids Res* 2005, 33, 5677; and above mentioned references) have contributed to understanding the interactions of AGAs with the rRNA target.

The above-mentioned studies have shown that the aminodeoxyglucopyranosyl ring I of 2-deoxystreptamine-derived AGAs binds to the rRNA in the same way regardless of whether the 2-deoxystreptamine is 4,5- or 4,6-disubstituted. According to the crystal structures of several AGAs, ring I intercalates into the bulge formed by A1408, A1492 and A1493, and the base pair C1409-G1491. Ring I stacks upon G1491 and forms a pseudo base pair with A1408 characterized by H-bonds from C(6')-OH to N(1) of A1408, and from C(5')-OH to N(6) of A1408. Additionally, ring I shows two non-specific interactions with the phosphate groups of the two flipped-out adenines 1492 and 1493: C(3')-OH forms an hydrogen bond with O2P of A1492, and C(4')-OH forms a hydrogen bond with O2P of A1493.

Neamine-based derivatives are currently under investigation for reducing bacterial) aminoglyoside resistance and for use as anti-HIV agents.

U.S. patent application 2006/0211634 A1 teaches the use of neamine-based compounds for inhibiting aminoglycoside-6"-N-acetyltransferases capable of reversing or inhibiting bacterial resistance to aminoglycoside antibiotics. These compounds are characterized by large substituents on the 6'position such as Coenzyme A. They are not suggested for use as antibiotics.

WO 2005/060573 teaches compositions for modulating the activity of a nucleic acid molecule comprising a peptide nucleic acid moiety conjugated to a neamine moiety. The document does not disclose antibiotic activity for these compositions.

Feng et al. (Angew. Chem. Int. Ed. 2005, 44, 6859-6862) discloses the regio- and chemoselective 6'-N-derivatisation of neamine-based aminoglycosides with coenzyme A resulting in bisubstrate inhibitors as probes for studying aminoglycoside 6'-N-acetyltransferases (AAC(6') inhibitors). The same authors (Feng et al., J. Med. Chem. 2006, 4, 5273-5281) describe second generation AAC(6') inhibitors based on neamine having long polypeptidic substituents in the 6' position.

Riguet et al. (Tetrahedron 60, 2004: 8053-8064) teach a route for preparing neamine-based derivatives with heterocyclic substituents bound by linker units for targeting HIV1 TAR RNA. Later the same authors teach (Bioorganic & Medicinal Chemistry Letters 15 (2005) 4651-4655) neamine-based dimers and trimers for targeting HIV-1 TAR RNA.

Due to their high toxicity and significant levels of antibiotic resistance neamine-based aminoglycosides are presently of limited use.

The object underlying the present invention is to provide novel and improved antimicrobial compounds that are not modified by common microbial resistance determinants and that target microbial, in particular bacterial 16S ribosomal RNA, i.e. the compounds do not target at all or target to a substantially less degree eukaryotic cytosolic and/or mitochiondrial ribosomes.

DESCRIPTION OF THE INVENTION

It was found that specific paromamine-based compounds selectively target microbial 16 S RNA.

In a first aspect the present invention relates to compounds of formula (I):

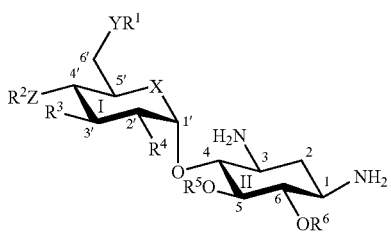

I wherein:
X, Y and Z denote in each case, independently of one another, —O—, —NH—, —S—, substituted or unsubstituted —CH$_2$— or a direct bond to R$^1$ and/or R$^2$;
R$^1$ and R$^2$ denote in each case, independently of one another, hydrogen, linear or branched, substituted or non-substituted alkyl, alkenyl, alkynyl, alkylidene, carbocycle, or YR$^1$ and ZR$^2$ together form a substituted or non-substituted cycloalkyl or a corresponding heterocyclic ring;
R$^3$ and R$^4$ denote in each case, independently of one another, hydrogen, amino or hydroxyl;
R$^5$ and R$^6$ denote in each case, independently of one another, hydrogen or glycosyl) residues;
and their diastereoisomers or enantiomers in the form of their bases or salts of physiologically acceptable acids.

In the context of the present invention it is understood that antecedent terms such as linear or branched, substituted or non-substituted indicate that each one of the subsequent terms is to be interpreted as being modified by said antecedent term. For example, the scope of the term "linear or branched, substituted or non-substituted alkyl, alkenyl, alkynyl, alkylidene, carbocycle" encompasses linear or branched, substituted or non-substituted alkyl; linear or branched, substituted or non-substituted alkenyl; linear or branched, substituted or non-substituted alkynyl; linear or branched, substituted or non-substituted alkylidene; and linear or branched, substituted or non-substituted carbocycle. For example, the term "C$_2$-C$_{12}$ alkenyl, alkynyl, or alkylidene" indicates the group of compounds having 2 to 12 carbons and alkenyl, alkynyl, or alkylidene functionality.

The compounds of the present invention are stable and resistant to bacterial degradation. However, it was demonstrated that some preferred embodiments of the compounds are more resistant against bacterial determinants than others.

In a preferred embodiment of the present invention the compounds of formula I are those, wherein R$^1$ and/or R$^2$, preferably R$^1$ and R$^2$ are not hydrogen. Said compounds demonstrate either a partial (R$^1$ and/or R$^2$≠H) or a complete (R$^1$ and R$^2$≠H) resistance against resistance determinants selected from the group consisting of ANT4'-OH, APH2''-OH/AAC6'-NH, AAC3-NH, ANT2''-OH, AAC6'-NH (Magnet et al., Chem. Rev. 2005).

In a more preferred embodiment the compounds of formula I are those, wherein YR$^1$ and ZR$^2$ together form a substituted or non-substituted cycloalkyl or a corresponding heterocyclic ring. Most preferred said cycloalkyl is an alkylidene, preferably an arylalkylidene (such as a benzylidene), most preferably an arylalkylidene substituted in the aryl ring.

In another preferred embodiment of the present invention the compounds of formula I are those, wherein R$^3$ and/or R$^4$, preferably R$^3$ and R$^4$ are hydrogen, i.e. they are not amino or hydroxyl. Said compounds demonstrate a resistance against one or both resistance determinants APH3' (if R$^3$ is H) and AAC2' (if R$^4$ is H).

In a most preferred embodiment, the compounds of formula I are those, wherein R$^1$ and/or R$^2$ are not hydrogen and R$^3$ and/or R$^4$ are hydrogen.

In a preferred embodiment of the present invention R$^1$ and R$^2$ denote in each case, independently of one another, hydrogen, linear or branched, substituted or non-substituted C$_1$-C$_{12}$ alkyl, C$_2$-C$_{12}$ alkenyl, alkynyl or alkylidene, C$_3$-C$_{12}$ cycloalkyl, C$_3$-C$_{20}$ aryl, preferably arylalkyl, C$_3$-C$_{20}$ heteroaryl or C$_3$-C$_{20}$ heterocyclic residues. More preferably, R$^1$ and R$^2$ denote in each case, independently of one another, linear or branched, substituted or non-substituted C$_1$-C$_8$ alkyl, C$_2$-C$_8$ alkenyl, alkynyl or alkylidene, C$_5$-C$_{12}$ cycloalkyl, C$_5$-C$_{12}$ cycloaryl, C$_5$-C$_{12}$ heteroaryl or C$_5$-C$_{12}$ heterocyclic residues. Most preferably, R$^1$ and R$^2$ denote in each case, independently of one another, linear or branched, substituted or non-substituted C$_1$-C$_4$ alkyl, C$_2$-C$_6$ alkenyl, alkynyl or alkylidene, C$_5$-C$_6$ cycloalkyl, C$_5$-C$_6$ cycloaryl, C$_5$-C$_6$ heteroaryl or C$_5$-C$_6$ heterocyclic residues.

In a preferred embodiment YR$^1$ is not NH$_2$. In another preferred embodiment ZR$^2$ is not OH.

It is also preferred that R$^1$ and/or R$^2$ do not comprise peptide nucleic acid moieties.

It is noted that increased size and steric hindrance in R$^1$ and/or R$^2$ can reduce selectivity and/or increase toxicity. Generally speaking, smaller R$^1$ and/or R$^2$ substituents are preferred for that reason.

Preferably, R$^1$ comprises, preferably is, an alkylaryl group, substituted or non-substituted in the aryl moiety, preferably a substituted or non-substituted (C$_1$-C$_5$ alkyl)aryl group and R$^2$ is H.

In another preferred embodiment R$^2$ is a linear or branched, substituted or non-substituted C$_1$-C$_7$ alkyl, C$_2$-C$_7$ alkenyl, alkynyl, or alkylidene, C$_3$-C$_7$ cycloalkyl, C$_3$-C$_7$ aryl, preferably aralkyl, C$_3$-C$_7$ heteroaryl or C$_3$-C$_7$ heterocyclic and R$^1$ is hydrogen.

In another preferred embodiment of the present invention R$^3$ is hydroxyl.

In another preferred embodiment of the present invention R$^4$ is amino.

In another preferred embodiment of the present invention R$^5$ is hydrogen.

In a preferred embodiment of the present invention R$^5$ is selected from the group consisting of mono- and polysaccharides. Preferably R$^5$ is a mono-, di- or trisaccharide, more preferably a mono- or disaccharide, most preferably a disaccharide, especially preferred a 2,6-diamino-2,6-dideoxy-β-L-idopyranosyl-(1→3)-β-D-ribofuranosyl moiety.

Preferably, R$^6$ is hydrogen.

In another preferred embodiment R$^6$ is selected from the group consisting of mono- and polysaccharides, preferably a mono-, di- or trisaccharide, more preferably a mono- or disaccharide, most preferably a monosaccharide, especially preferred a 3-amino-3-deoxy-α-D-glucopyranosyl moiety.

In another preferred embodiment $R^6$ is a 2,6-diamino-2,6-dideoxy-β-L-idopyranosyl-(1→3)-β-D-ribofuranosyl moiety.

In another more preferred embodiment $YR^1$ and $ZR^2$ together form a substituted or non-substituted cycloalkyl or a corresponding heterocyclic ring. Preferably, the ring formed by $YR^1$ and $ZR^2$ and ring I of formula I is a five or six-membered ring, more preferably a six-membered ring.

Most preferably, $YR^1$ and $ZR^2$ together form a 6-membered 4',6'-cycloalkyl or substituted 4',6'-cycloalkyl ring.

In another preferred embodiment Y and Z, preferably X, Y and Z are oxygen.

In a more preferred embodiment compounds of formula (I) above are compounds of formula (II) below:

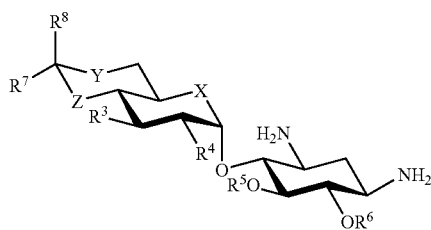

herein:

X, Y and Z denote in each case, independently of one another, —O—, —NH—, —S—, substituted or non-substituted —$CH_2$—;

$R^7$ denotes hydrogen, linear or branched, substituted or non-substituted alkyl, alkenyl, alkynyl, alkylidene, or carbocycle;

$R^8$ denotes hydrogen, OH with the proviso that the compound is stable, $NH_2$, $NR_aR_b$, SH, $SR_a$, $OR_a$ or a linear or branched, substituted or non-substituted $C_1$-$C_8$ alkyl, preferably $C_1$-$C_4$ alkyl, wherein $R_a$ and $R_b$ are in each case, independently of one another, $C_1$-$C_8$ alkyl, preferably $C_1$-$C_4$ alkyl;

$R^3$ denotes hydrogen, amino or hydroxyl, preferably amino or hydroxyl;

$R^4$ denotes hydrogen, amino or hydroxyl, preferably amino or hydroxyl;

$R^5$ denotes hydrogen, a mono- or polysaccharide, preferably a mono-, di- or trisaccharide, more preferably a mono- or disaccharide, most preferably a disaccharide, especially preferred a 2,6-diamino-2,6-dideoxy-β-L-idopyranosyl-(1→3)-β-D-ribofuranosyl moiety;

$R^6$ denotes hydrogen, a mono- or polysaccharide, preferably a mono-, di- or trisaccharide, more preferably a mono- or disaccharide, most preferably a monosaccharide, especially preferred a 3-amino-3-deoxy-α-D-glucopyranosyl moiety.

In formula II X, Y and Z are preferably all oxygen.

In a preferred embodiment of formula II $R^7$ denotes hydrogen, a linear or branched, substituted or non-substituted $C_1$-$C_8$ alkyl, $C_3$-$C_8$ cycloalkyl, $C_5$-$C_{20}$ aryl, $C_5$-$C_{20}$ heteroaryl, preferably $C_5$-$C_{12}$ heteroaryl.

In a more preferred embodiment of formula II $R^7$ denotes linear, substituted or non-substituted $C_1$-$C_8$ alkyl, preferably substituted linear $C_1$-$C_3$ alkyl, more preferably aryl-substituted $C_1$-$C_3$ alkyl; substituted or non-substituted $C_3$-$C_8$ cycloalkyl, $C_5$-$C_{12}$ aryl, $C_5$-$C_{12}$ heteroaryl, preferably substituted $C_5$-$C_{12}$ heteroaryl.

In another more preferred embodiment $R^7$ denotes $C_5$-$C_{12}$ aryl or heteroaryl, preferably a ($C_1$-$C_7$ alkyl)aryl group.

In a more preferred embodiment of formula II $R^7$ is an aryl substituted ethyl group.

In another preferred embodiment compounds of the present invention of formula I or II comprise one or more halogens, preferably one halogen, preferably a chlorine, bromine, fluorine or iodine, more preferably a fluorine. For compounds of formula II it is preferred that $R^7$ comprises a halogen, preferably a chlorine, bromine, fluorine or iodine, more preferably a fluorine.

For compounds of formula II it is preferred that $R^8$ is selected from the group consisting of hydrogen, halogen or linear or branched, substituted or non-substituted $C_1$-$C_8$ alkyl, preferably $C_1$-$C_4$ alkyl, most preferably hydrogen.

For compounds of formula II $R^5$ or $R^6$ is preferably hydrogen.

For compounds of formula II $R^6$ is preferably a 2,6-diamino-2,6-dideoxy-β-L-idopyranosyl-(1→3)-β-D-ribofuranosyl moiety.

In a further preferred embodiment of the invention relating to compounds of formula I and/or II $R^1$ and/or $R^2$, preferably both, denote a linear or branched, substituted or non-substituted alkyl or cycloalkyl, wherein one or more of the carbon atoms are replaced, independently of one another, by oxygen, sulfur or nitrogen atoms.

In a most preferred embodiment the paromamine-based compounds of the present invention are selected from the group consisting of 4',6'-O-benzylideneparomomycin,
4',6'-O-p-methoxybenzylideneparomomycin,
4',6'-O-m-methoxybenzylideneparomomycin tetraacetate,
4',6'-O-o-methoxybenzylideneparomomycin,
4',6'-O-2,5-dimethoxybenzylideneparomomycin,
4',6'-O-p-nitrobenzylideneparomomycin,
4',6'-O-m-nitrobenzylideneparomomycin triacetate,
4',6'-O-p-chlorobenzylideneparomomycin,
4',6'-O-3,5-dichlorobenzylideneparomomycin,
4',6'-O-p-cyanobenzylideneparomomycin,
4',6'-O-p-phenylbenzylideneparomomycin,
4',6'-O-p-fluorobenzylideneparomomycin,
4',6'-O-3,5-dimethoxybenzylideneparomomycin,
4',6'-O-3,4,5-trimethoxybenzylideneparomomycin,
4',6'-O-m-chlorobenzylideneparomomycin,
4',6'-O-o-nitrobenzylideneparomomycin,
4',6'-O-p-trifluoromethylbenzylideneparomomycin,
4',6'-O-p-dimethylaminobenzylideneparomomycin,
4',6'-O-1-naphthylideneparomomycin,
4',6'-O-2-naphthylideneparomomycin,
4',6'-O-2-furanylideneparomomycin,
4',6'-O-2-thiophenylideneparomomycin and
4',6'-O-ethylideneparomomycin,
4',6'-O-(2-phenyl)-ethylideneparomomycin,
4',6'-O-(3-phenyl)-propylideneparomomycin,
4',6'-O-(3-phenyl)-propenylideneparomomycin,
4',6'-O-cyclohexylmethylideneparomomycin,
4'-O-benzylparomomycin,
6'-O-benzylparomomycin,
4'-p-chlorobenzyl paromomycin,
4'-p-(trifluoromethyl)benzylparomomycin,
4'-benzyloxymethylparomomycin and
4'-p-methoxybenzylparomomycin.

DEFINITIONS

In all compounds disclosed herein, in the event that the nomenclature conflicts with the structure, it shall be understood that the compound is defined by the structure.

The invention includes all compounds described herein containing one or more asymmetric carbon atoms that may occur as racemates and racemic mixtures, single enantiomers, diastereoisomeric mixtures and individual diastereoisomers. All such isomeric forms of these compounds are expressly included in the present invention. Each stereogenic carbon may be in the R or S configuration or a combination of configurations. It is understood that the stereogenic structure of the paromamine core of the compounds of the invention is fixed as shown in formulas 1, I and II.

Some of the compounds of the general formulas (I) and (II) disclosed herein can exist in more than one tautomeric form. The present invention includes all such tautomers.

All terms as used herein shall be understood by their ordinary meaning as known in the art.

The term "heteroatom" as used herein shall be understood to mean atoms other than carbon and hydrogen such as and preferably O, N, S and P.

The terms alkyl, alkenyl, alkynyl, alkylidene, etc. shall be understood as encompassing linear as well as branched forms of carbon-containing chains where structurally possible. In these carbon chains one or more carbon atoms can be optionally replaced by heteroatoms, preferably by O, S or N. If N is not substituted it is NH. The heteroatoms may replace either terminal or internal carbon atoms within a linear or branched carbon chain. Such groups can be substituted as herein described by groups such as oxo to result in definitions such as but not limited to alkoxycarbonyl, acryl, amido and thioxo.

The term "carbocycle" shall be understood to mean an aliphatic hydrocarbon radical containing from 3 to 20, preferably from 3 to 12 carbon atoms, more preferably 5 or 6 carbon atoms. Carbocylces include hydrocarbon rings containing from 3 to 10 carbon atoms. These carbocycles may be either aromatic or non-aromatic systems. The non-aromatic ring systems may be mono or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, and benzocycloheptenyl. Certain terms for cycloalkyl such as cyclobutanyl and cyclobutyl shall be used interchangeably.

The term "cycloalkyl" shall be understood to mean aliphatic hydrocarbon-containing rings having from 3 to 12 carbon atoms. These non-aromatic ring systems may be mono- or polyunsaturated, i.e. the term encompasses cycloalkenyl and cycloalkynyl. The cycloalkyl may comprise heteroatoms, preferably O, S or N, and be substituted or non-substituted. Preferred and non-limiting cycloalkyls include cyclopropyl, cyclobutyl, cyclopentyl, cyclopentenyl, cyclohexyl, cyclohexenyl, cycloheptanyl, cycloheptenyl, benzocyclobutanyl, benzocycloheptanyl and benzocycloheptenyl.

The term "heterocyclic" refers to a stable non-aromatic, preferably 3 to 20 membered, more preferably 3-12 membered, most preferably 5 or 6 membered, monocyclic or multicyclic, preferably 8-12 membered bicyclic, heteroatom-containing cyclic radical, that may be either saturated or unsaturated. Each heterocycle consists of carbon atoms and one or more, preferably 1 to 4 heteroatoms chosen from nitrogen, oxygen and sulphur. The heterocyclic residue may be bound to the remaining structure of the complete molecule by any atom of the cycle, which results in a stable structure. Exemplary heterocycles include but are not limited to pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo[7.3.1.0-2,7]tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydro-pyrimidonyl, pentamethylene sulphide, pentamethylene sulfoxide, pentamethylene sulfone, tetramethylene sulphide, tetramethylene sulfoxide and tetramethylene sulfone.

The term "aryl" as used herein shall be understood to mean an aromatic carbocycle or heteroaryl as defined herein. Each aryl or heteroaryl unless otherwise specified includes its partially or fully hydrogenated derivative. For example, quinolinyl may include decahydroquinolinyl and tetrahydroquinolinyl; naphthyl may include its hydrogenated derivatives such as tetrahydronaphthyl. Other partially or fully hydrogenated derivatives of the aryl and heteroaryl compounds described herein will be apparent to one of ordinary skill in the art. Naturally, the term encompasses aralkyl and alkylaryl, both of which are preferred embodiments for practicing the compounds of the present invention. For example, the term aryl encompasses phenyl, indanyl, indenyl, dihydronaphthyl, tetrahydronaphthyl, naphthyl and decahydronaphthyl.

The term "heteroaryl" shall be understood to mean an aromatic $C_3$-$C_{20}$, preferably 5-8 membered monoxyclic or preferably 8-12 membered bicyclic ring containing 1-4 heteroatoms such as N, O and S. Exemplary heteroaryls comprise aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazole[3,4-b]pyridinyl, tubercidinyl, oxazo[4,5-b]pyridinyl and imidazo[4,5-b]pyridinyl.

Terms which are analogues of the above cyclic moieties such as aryloxy or heteroaryl amine shall be understood to mean an aryl, heteroaryl, heterocycle as defined above attached to its respective group.

As used herein, the terms "nitrogen" and "sulphur" include any oxidized form of nitrogen and sulphur and the quaternized form of any basic nitrogen as long as the resulting compound is chemically stable. For example, for an —S—$C_{1-6}$ alkyl radical shall be understood to include —S(O)—$C_{1-6}$alkyl and —S(O)$_2$—$C_{1-6}$ alkyl.

The compounds of the invention are only those which are contemplated to be 'chemically stable' as will be appreciated by those skilled in the art. For example, compounds having a 'dangling valency' or a 'carbanion' are not compounds contemplated by the inventive disclosed herein.

The above described compounds have demonstrated a strong and antimicrobial, in particular antibacterial, 16 S RNA specific activity making them particularly useful for preparing medicaments lacking toxicity due to the essential lack of activity in eukaryotic cells, i.e. no interaction with eukaryotic cytosolic and/or mitochondrial RNA.

Because of the above described highly selective activity another aspect of the present invention relates to the use of one or more compounds of the invention for preparing a medicament.

In a preferred embodiment one or more compounds of the present invention are used for preparing a medicament for the treatment and/or prevention of a microbial, preferably a bacterial, infection.

In a further preferred embodiment the invention relates to the use of one or more compounds according to the invention for preparing a medicament for the treatment and/or prevention of leishmaniasis.

In another preferred embodiment the invention relates to the use of one or more compounds according to the invention for preparing a medicament for the treatment and/or prevention of trypanosomiasis.

A further aspect of the present invention concerns pharmaceutical compositions, comprising as active substance one or more compounds of the present invention or pharmaceutically acceptable derivatives or prodrugs thereof, optionally combined with conventional excipients and/or carriers.

Medical Use and Pharmaceutical Compositions

The invention includes pharmaceutically acceptable derivatives of compounds of formulae (I) and (II). A "pharmaceutically acceptable derivative" refers to any pharmaceutically acceptable salt or ester or any other compound which, upon administration to a patient, is capable of providing (directly or indirectly) a compound of the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I) and (II). Preferred embodiments relate to pharmaceutically acceptable derivatives of compounds of formulas (I) and (II) that are hydrates.

Pharmaceutically acceptable salts include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g. magnesium), ammonium and N—$(C_1\text{-}C_4\text{alkyl})_4^+$ salts.

In addition, the scope of the invention also encompasses prodrugs of compounds of the formulas (I) and (II). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention have demonstrated a selective inhibition of the bacterial ribosome. These drugs do not affect the eukaryotic ribosome because they do not target eukaryotic mitochondrial or cytosolic 16S ribosomal RNA as demonstrated in tests with genetically engineered ribosomes carrying eukaryotic 16 S RNA nucleotide positions.

Hence, in a further aspect the present invention is directed to the use of one or more compounds according to the invention for preparing a medicament. Preferably, the compounds of the invention are used for preparing a medicament for the treatment and/or prevention of a bacterial infection.

In the above respect the present invention also relates to a pharmaceutical composition, comprising as active substance one or more compounds according to the invention or pharmaceutically acceptable derivatives or prodrugs thereof, optionally combined with conventional excipients and/or carriers.

Methods of Use

For therapeutic or prophylactic use the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically, or by inhalation. The preferred modes of administration are oral and intravenous.

The compounds may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (2) or (3) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminium stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical *Dosage Forms and Drug Delivery Systems,* $5^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from about 1-100 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

For example, the compounds of the present invention can be administered the same way as paromomycin and other paromamine compounds. They may be administered orally in the treatment of intestinal infections or parenterally for visceral and topically for cutaneous leishmaniasis.

Preferably, the compounds of the invention are administered as sulfate salts. In the case of intestinal amoebiasis the oral dosage for both adults and children may be 5 to 70, preferably 15 to 50, more preferably 25 to 35 mg compound of the invention per kg body weight daily, administered in three doses with meals for five to ten days. In the case of hepathic coma, the oral daily dosage is 4 g in divided doses given at regular intervals for 5 to 6 days.

Compounds of the invention may be formulated into capsules the same way paromomycin is formulated (e.g. Humatin®, Parke-Davis). Each capsule may contain 100 to 500, preferably 150 to 300, more preferably 200 to 250 mg of a compound of the invention. For example, nonmedicinal ingredients in capsules for the compounds of the present invention are—capsule shell: D&C yellow No. 10, FD&C blue No. 1, FD&C red No. 3, FD&C yellow No. 6, gelatin and titanium dioxide. Bottles of 100. (see also *Martindale: the complete drug reference*, 34th Edition, 2005, Pharmaceutical Press, p 612.)

It is emphasized that compounds of the present invention may be administered in higher dosages than paromomycin or other unspecific antibiotics because the compounds of the invention are selective for microbial, in particular bacterial, ribosomes and spare eukaryotic ribosomes, thus lacking serious side effects.

Methods for Preparing Compounds of the Invention

The compounds of the invention can be prepared by standard methods well known to) those of skill in the art, in particular in the art of organic and glycoside chemistry. General schemes and specific examples for their preparation are provided for in the examples below which are by no means considered limiting but meant as illustrative only.

In the following a preferred method for preparing compounds of the invention is provided which is also considered the best mode for practicing the invention.

In a further aspect the invention relates to a method for preparing a compound according to the invention, comprising one or more of the following steps:

a) providing a compound according to the formula III:

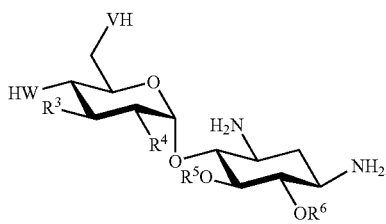

III wherein:
V and W denote in each case, independently of one another, —O—, —NH— and —S—;
$R^3$ and $R^4$ denote in each case, independently of one another, hydrogen, amino or hydroxyl;
$R^5$ and $R^6$ denote in each case, independently of one another, hydrogen or glycosyl residues;
b) protecting one or more, preferably all, of the amino groups;
c) optionally protecting one or more, preferably all, of the hydroxy groups;
d1) selectively transforming the optionally protected 4'- and/or 6'-hydroxy groups to $YR^1$ and/or $ZR^2$-groups of formula I or the ring system of formula II; or
d2) selectively deprotecting the protected 4'- and/or 6'-hydroxy groups and selectively transforming the deprotected 4'- and/or 6'-hydroxy groups to $YR^1$ and/or $ZR^2$-groups of formula I or the ring system of formula II;
e) deprotecting the one or more amino groups;
f) deprotecting the one or more hydroxy groups;
wherein the order of steps b) and c) as well as e) and f) may be reversed, the order of b) and c) as well as e) and f) being preferred.

Regarding the option of step c) it is noted that for preparing some compounds of the invention, e.g. compounds of formula II, it may not be necessary to protect one or more of the hydroxyl groups. This is especially true when a dioxane, dioxane derivative or other arylalkylidene (such as benzylidene) moiety is introduced to generate a compound of formula II. In that case the moiety introduced in step d1) may already function as a protecting group.

When V and/or W is a divalent sulfur atom, $R^1$ and/or $R^2$-groups of formula I are introduced by reaction with an appropriate electrophile, such as a halogen derivative, or a sulfonate. Alternatively, the same resulting $YR^1$ and/or $ZR^2$ may be introduced, directly or indirectly, from an optionally protected compound of formula III where VH and WH denote independently of one another a hydroxy group. The ring system of formula II may be introduced by acetal formation with $R^7CHO$ or $R^7CH(OR^a)(OR^b)$, wherein $R^a$ and $R^b$ are alkyl residues, preferably methyl, in the presence of a suitable organic and/or inorganic acid and, if necessary, in a suitable solvent, or by reaction with

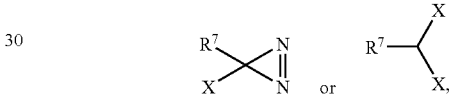

wherein X is a leaving group, preferably a halogen atom, more preferably bromine, in the presence of a base and, if necessary, in a suitable solvent.

It is noted that the protecting and deprotecting steps for amino and/or hydroxyl groups can be accomplished by any suitable reactions that are routinely available to the skilled person and that are not detrimental to the compounds of the invention.

Preferably the amino groups are protected by converting them to azido, carbamoyl or N-acylamino groups. More preferably the amino groups are protected by converting them to azido groups by diazo transfer.

Preferably the hydroxy groups are protected by converting them to ethers, preferably alkyl and/or silyl ethers, and/or esters, preferably sulfonates or acetals. More preferred the hydroxy groups are protected as acetoxy groups by converting them with an acyl transfer reagent, preferably acetic anhydride, preferably in the presence of bases and/or catalysts.

For the acetoxy groups it is preferred that they are deprotected by base- or acid-catalyzed hydrolysis, or other solvolysis, or by reduction with a hydride donor, such as diisobutyl aluminum hydride, $LiAlH_4$, or $LiBH_4$.

In another preferred embodiment 4',6'-acetals of formula III are prepared by reaction of a hydroxy compound of formula III with $R^7CHO$ or $R^7CH(OR^a)(OR^b)$, wherein $R^a$ and $R^b$ are alkyl residues, preferably methyl, in the presence of a suitable organic and/or inorganic acid and, if necessary, in a suitable solvent.

In another preferred embodiment 4',6'-acetals of formula III are prepared by reaction of a hydroxy compound of formula III with

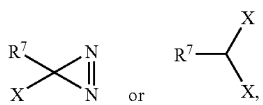

wherein X is a leaving group, preferably a halogen atom, more preferably bromine, in the presence of a base and, if necessary, in a suitable solvent.

Azido groups are preferably deprotected by a method selected from the group consisting of:
reductive hydrogenation, preferably hydrogen in the presence of a suitable catalyst, such as, e.g. Pd, Pd(OH)$_2$, Rh, or Pt;
by hydrogen and nickel boride;
reaction with a hydride reagent, preferably a borohydride or an aluminum hydride, electron transfer, preferably by reaction with hydrogen sulfide, a thiol, or a dithiol in the presence of base,
a metallic reduction, such as by Zn or Na, or Na-amalgam in the presence of an alcohol, and
treatment with a phosphine reagent, preferably with trimethylphosphine (Staudinger reaction) followed by hydrolysis (see Staudinger and Meyer, Helv. Chim. Acta 1919, 2, 635; Golobov et al., Tetrahedron, 1981, 37, 437; and Scriven et al., Chem. Rev., 1988, 88, 297; and as described in S. D. Burke and R. L. Danheiser, ed. "Oxidizing and Reducing Agents", J. Wiley, Chichester, 1999).

In a preferred embodiment the present invention relates to a method, wherein 4'- and 6'-hydroxy groups are selectively deprotected.

In another preferred embodiment the 4'- and 6'-hydroxy groups are protected as a benzylidene acetal. Said 4',6'-benzylidene acetal is preferably deprotected by a method selected from the group consisting of catalytic hydrogenation, Birch reduction and acid-catalyzed hydrolysis.

In a preferred embodiment the method of the invention comprises the regioselective reductive cleavage of the 4',6'-acetal to result in the more hindered ether derivative by reaction with a suitable hydride reagent, preferably the borane-dimethyl sulfide complex in the presence of a suitable Lewis acid.

In another preferred embodiment the method of the invention comprises the regioselective reductive cleavage of the 4',6'-acetal to result in the less hindered ether derivative by reaction with a suitable hydride reagent, preferably sodium cyanoborohydride in the presence of a suitable acid.

In another preferred embodiment hydroxy groups in the compounds of formula III are protected as benzyloxy groups, the benzyl part preferably being substituted or unsubstituted arylmethyl or heteroarylmethyl. Most preferred the benzyloxy group is a p-methoxybenzyloxy group, preferably being introduced by reaction of a compound of formula III with a suitable p-methoxybenzyl transfer reagent such as a p-methoxybenzyl halide in the presence of a suitable base or acid. In a preferred embodiment the p-methoxybenzyloxy groups are deprotected by oxidative cleavage with a suitable reagent, preferably with dichlorodicyanoquinone.

In amore preferred embodiment the method of the invention requires that the primary 6'-hydroxy group of formula III is selectively protected as an ether, preferably an alkyl or silyl ether, or an ester, preferably a sulfonate or an acetal. It is most preferred that the primary 6'-hydroxy group is a monomethoxytrityloxy group, preferably introduced into compounds of formula III by reaction with a suitable monomethoxytrityl transfer reagent such as a monomethoxytrityl halide in the presence of a suitable base.

Last but not least, it is preferred that the 4'-hydroxy group is protected as an ether, preferably by reaction with a suitable alkoxy transfer reagent, preferably an alkyl halide in the presence of a suitable base.

FIGURES

FIG. 1: illustrates the strategy for deletion of rRNA operon rrnB according to example 3. Open arrows represent rRNA genes; P and T the promoter and termination sequences, respectively. Solid arrows indicate the open reading frames upstream and downstream of rrnB. Hatched rectangles represent antibiotic resistance cassettes, the stippled arrow the sacB gene. Broken lines indicate possible crossover sites between homologous sequences in the replacement vector (A) and the chromosomal target site (B). Following plasmid integration into the rrnB 5'-flanking region (C), a second crossover event) between the homologous 3'-flanking sequences resolves the chromosomal tandem repeat to the deletion of rrnB (D).

Figure 2:
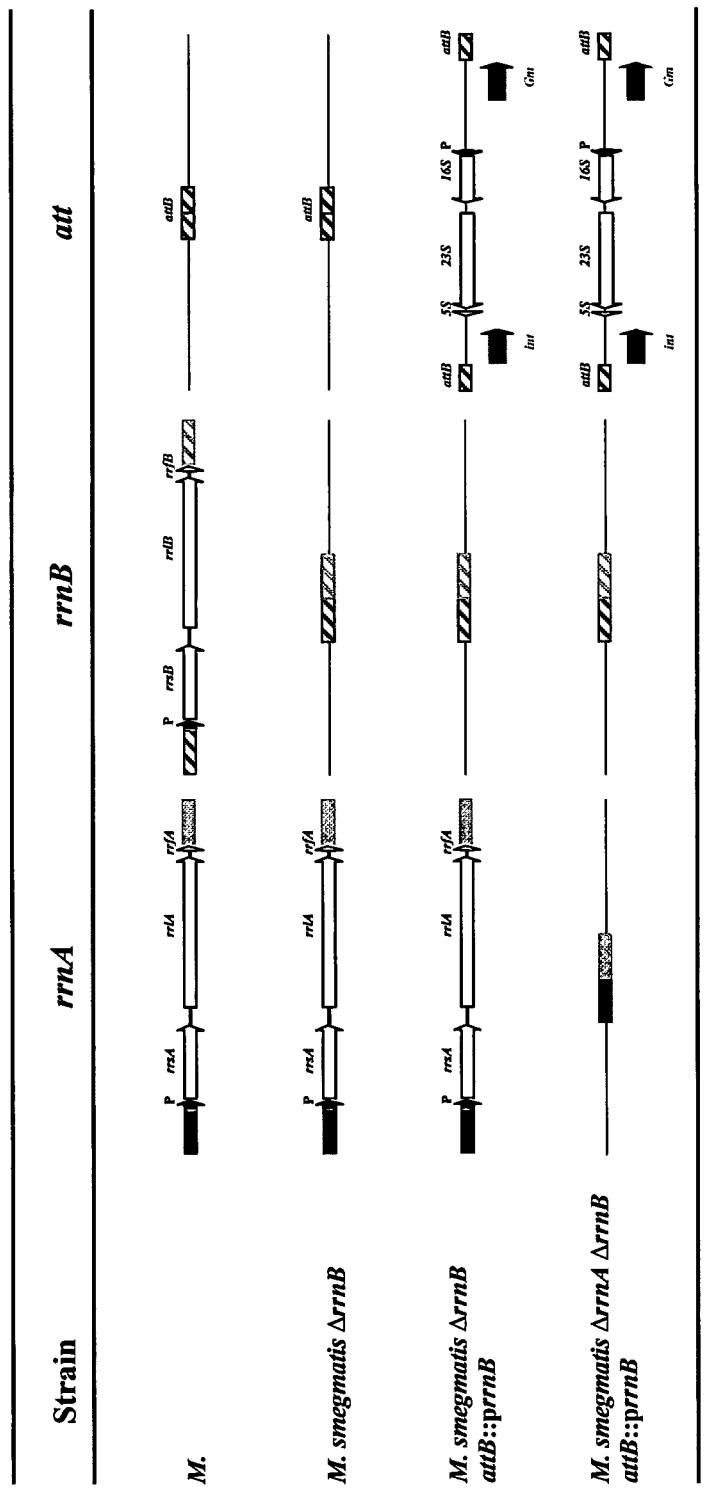

FIG. 2 illustrates the sequential strategy for the generation of *M. smegmatis* ΔrrnA ΔrrnB attB::prrnB according to example 3. Following deletion of chromosomal rrnB, a complementation vector carrying a functional rrnB operon is introduced to the chromosomal attB site. Subsequent deletion of rrnA results in strain *M. smegmatis* ΔrrnA ΔrrnB attB::prrnB, in which ribosomal RNA is exclusively transcribed from the plasmid.

In the following the subject-matter of the invention will be described in more detail referring to specific embodiments which are not intended to be construed as limiting to the scope of the invention.

Brauchen wir diese Liste wirklich? Die meisten Abkürzungen sind dem Fachmann/Fachfrau geläufig. Ich habe schon mal ein paar gestrichen, die wir mit Sicherheit nicht brauchen.

LIST OF ABBREVIATIONS ax=axial, c=concentration, DDQ=dichlorodicyanoquinone, dec.=decomposition, eq=equatorial, equ.=equivalent, ESI=electrospray ionisation, FC=flash chromato-graphy, HR=high resolution, HSQC=heteronuclear single quantum coherence, MMTr=monomethoxytrityl, —(X Å) MS=molecular sieves, PMB=4-methoxybenzyl, Tf=trifluoromethanesulfonyl, Ts=4-toluenesulfonyl.

EXAMPLES

Example 1

Materials and Methods

Solvents were freshly distilled: THF from Na and benzophenone, CH$_2$Cl$_2$, MeOH, pyridine, Et$_3$N from CaH$_2$. Reactions were carried out under nitrogen, unless stated otherwise. Qual. TLC: precoated silica-gel glass plates (Merck silica gel 60 F$_{254}$); detection by heating with 'mostain' (400 ml of 10% H$_2$SO$_4$ soln., 20 g of (NH$_4$)$_6$Mo$_7$O$_{24}$.6H$_2$O, 0.4 g of Ce(SO$_4$)$_2$). Flash chromatography (FC): silica gel Merck 60 (0.063-0.20). M.p.'s uncorrected. Optical rotations: 1-dm cell at 25°, 589 nm. FT-IR spectra: ATR, absorption in cm$^{-1}$. $^1$H- and $^{13}$C-NMR spectra: chemical shifts δ in ppm rel. to TMS as external standard, and coupling constants J in Hz. HR-ES-MS or HR-MALDI-MS: in gentisic acid (=2,5-dihydroxybenzoic acid, DHB) matrix.

Synthesis of Acetals
Scheme 1
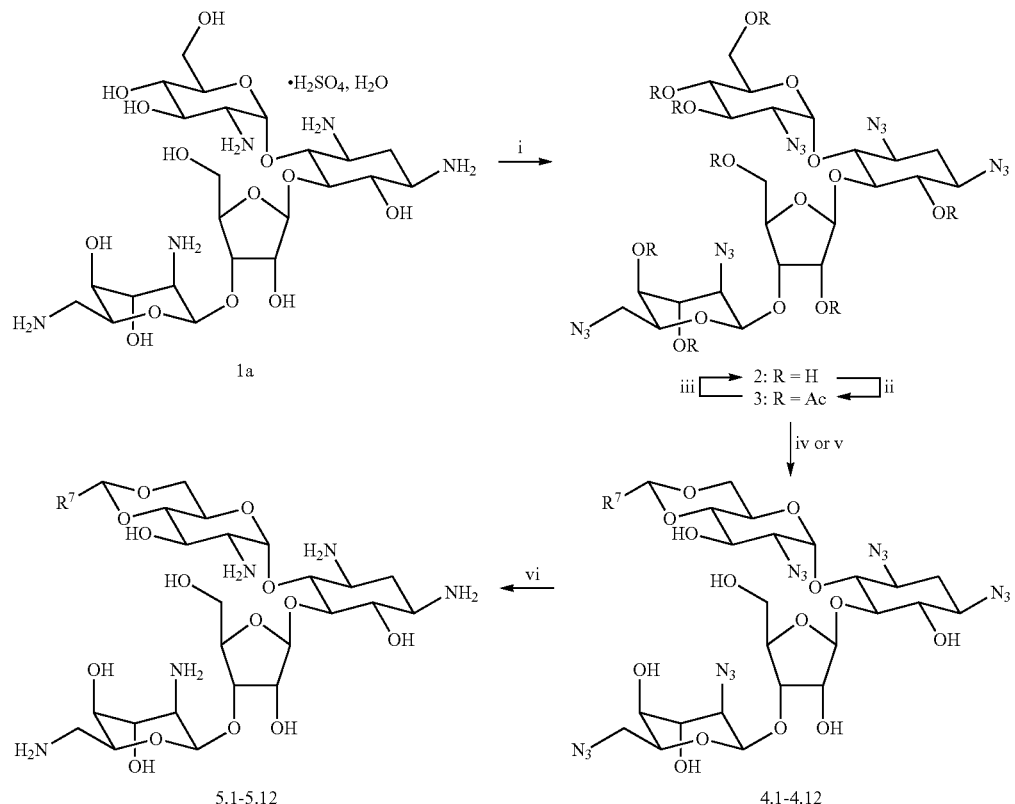
i) TfN$_3$, CuSO$_4$, $^t$BuOK, H$_2$O/$^t$BuOH/CH$_2$Cl$_2$ 1/2/1, 23° C., 18 h; ii) Ac$_2$O, DMAP, Pyr, Ar, 23°, 18 h; iii) NaOMe, MeOH, 23°, 12 h; iv) R$^7$ = PhCHO, HCO$_2$H, -5°-0°, Ar, 24 h, 85%; v) R$^7$CH(OMe)$_2$, TsOH•H$_2$O, DMF, N$_2$, 23°-65°; vi) 0.1M aq. NaOH, 1M PMe$_3$ in THF, THF, N$_2$, 65°.
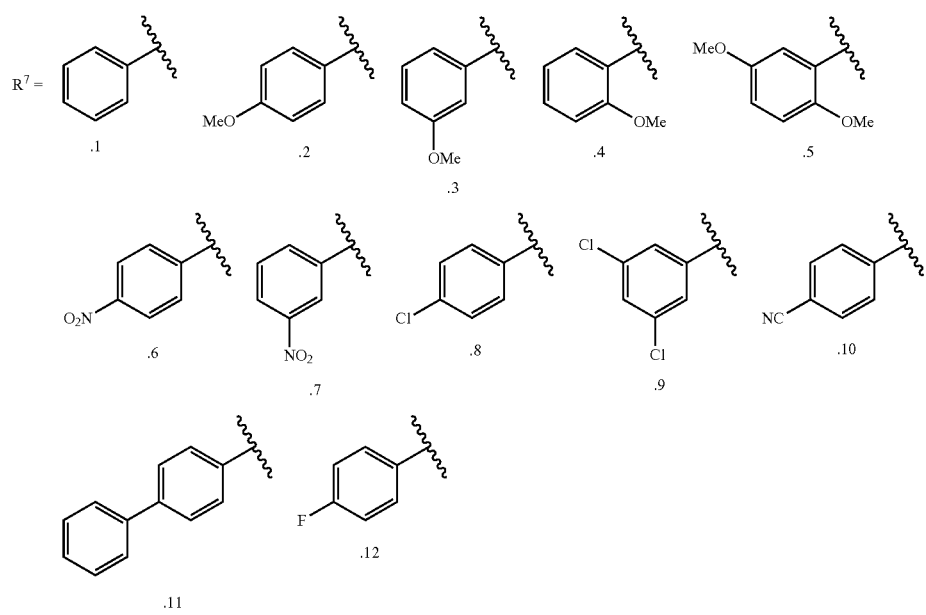

Compounds 2, 3, 4.1 were synthesized as described in *Helv Chim Acta* 2005, 88, 2967.

Typical Procedure for the Formation of the Acetals 4.2-4.12 (Scheme 1).

Under $N_2$ a soln. of 2 in DMF was treated with a solution of the corresponding dimethylacetal of $R^7CHO$ (5 equ.) in DMF and $TsOH.H_2O$ (0.5 equ.) and, stirred at 25° or at 65°. The mixture was diluted with AcOEt and washed with 0.1 M aq. NaOH. The aqueous layer was extracted twice with AcOEt. The combined org. layers were washed with brine, dried ($MgSO_4$), filtered, and evaporated. FC (Hexane/AcOEt 8:2, $CHCl_3$/AcOEt 1:1→$CHCl_3$/AcOEt/$CH_3OH$ 6:6:0.25) gave 4.2-4.12.

1,3,2',2''',6'''-Pentadeamino-1,3,2',2''',6'''-pentaazido-4',6'-O-p-Methoxybenzylideneparomomycin (4.2)

Reaction of 71 mg of 2 gave 57 mg of 4.2 (69%). White solid. $R_f$ ($CHCl_3$/AcOEt/MeOH 3:3:0.5) 0.46. $[\alpha]_D^{29}$= +112.5 (c=0.29, $CH_3OH$). HR-Maldi-MS: 902.2569 (22, [M+K]$^+$, $C_{31}H_{41}N_{15}O_{15}^+$; calc. 902.2544); 887.2817 (39, [M+Na+H]$^+$, $C_{31}H_{42}N_{15}NaO_{15}^+$; calc. 887.2883); 886.2783 (100, [M+Na]$^+$, $C_{31}H_{41}N_{15}NaO_{15}^+$; calc. 886.2799). Anal. calc. for $C_{31}H_{41}N_{15}O_{15}.CH_3OH$ (895.79): C, 42.91; H, 5.06; N, 23.45. found: C, 43.31; H, 5.00; N, 23.14.

1,3,2',2''',6'''-Pentadeamino-1,3,2',2''',6'''-pentaazido-4',6'-O-m-methoxybenzylideneparomomycin (4.3)

Reaction of 101 mg of 2 gave 47 mg of 4.3 (40%). White solid. $R_f$($CHCl_3$/AcOEt/MeOH 3:3:0.5) 0.45. $[\alpha]_D^{29}$=+98.2 (c=0.17, $CH_3OH$). HR-Maldi-MS: 863.2932 (33, [M]$^+$, $C_{31}H_{41}N_{15}O_{15}^+$; calc. 863.2907); 862.2849 (88, [M–H]$^+$, $C_{31}H_{40}N_{15}O_{15}^+$; calc. 862.2834). Anal. calc. for $C_{31}H_{41}N_{15}O_{15}.CH_3CO_2CH_2CH_3$ (951.85): C, 44.16; H, 5.19; N, 22.07. found: C, 43.83, H, 5.32, N, 21.71.

1,3,2',2''',6'''-Pentadeamino-4,3,2',2''',6'''-pentaazido-4',6'-O-o-methoxybenzylideneparomomycin (4.4)

Reaction of 99 mg of 2 gave 76 mg of 4.4 (66%). White solid. $R_f$ ($CHCl_3$/AcOEt/MeOH 3:3:0.5) 0.40. $[\alpha]_D^{29}$= +120.6 (c=0.28, $CH_3OH$). HR-Maldi-MS: 887.2812 (33, [M+Na+H]$^+$, $C_{31}H_{43}N_{15}NaO_{15}^+$; calc. 887.2883); 886.2784 (100, [M+Na]$^+$, $C_{31}H_{42}N_{15}NaO_{15}^+$; calc. 886.2799). Anal. calc. for $C_{31}H_{41}N_{15}O_{15}.CH_3OH$ (895.79): C, 42.91; H, 5.06; N, 23.45. found: C, 43.01; H, 5.23; N, 23.37.

1,3,2',2''',6'''-Pentadeamino-1,3,2',2''',6'''-pentaazido-4',6'-O-2,5-dimethoxybenzylideneparomomycin (4.5)

Reaction of 119 mg of 2 gave 104 mg of 4.5 (73%). White solid. $R_f$($CHCl_3$/AcOEt/MeOH 3:3:0.5) 0.54. $[\alpha]_D^{29}$=+105.0 (c=0.295, $CH_3OH$). HR-Maldi-MS: 917.2917 (40, [M+Na+H]$^+$, $C_{32}H_{44}N_{15}NaO_{16}^+$; calc. 917.2988); 916.2887 (100, [M+Na]$^+$, $C_{32}H_{43}N_{15}NaO_{16}^+$; calc. 916.2904). Anal. calc. for $C_{32}H_{43}N_{15}O_{16}.CH_3OH$ (925.82): C, 42.81; H, 5.12; N, 22.69. found: C, 42.93; H, 5.34; N, 22.34.

1,3,2',2''',6'''-Pentadeamino-1,3,2',2''',6'''-pentaazido-4',6'-O-p-nitrobenzylideneparomomycin (4.6)

Reaction of 49 mg of 2 gave 104 mg 4.6 (35%). White solid. $R_f$ ($CHCl_3$/AcOEt/$CH_3OH$ 3:3:0.5) 0.36. HR-Maldi-MS: 878.2619 (39, [M]$^+$, $C_{30}H_{38}N_{16}O_{16}^+$; calc. 878.2652); 877.2570 (100, [M–H]$^+$, $C_{30}H_{37}N_{16}O_{16}^+$; calc. 877.2573).

1,3,2',2''',6'''-Pentadeamino-1,3,2',2''',6'''-pentaazido-4,6'-O-m-nitrobenzylideneparomomycin (4.7)

Reaction of 100 mg of 2 gave 29 mg of 4.7 (26%). White solid. $R_f$ ($CHCl_3$/AcOEt/MeOH 3:3:0.5) 0.36. HR-Maldi-MS: 878.2604) (44, [M]$^+$, $C_{30}H_{38}N_{16}O_{16}^+$; calc. 878.2652); 877.2561 (100, [M–H]$^+$, $C_{30}H_{37}N_{16}O_{16}^+$; calc. 877.2573).

1,3,2',2''',6'''-Pentadeamino-1,3,2',2''',6'''-pentaazido-4',6'-O-p-chlorobenzylideneparomomycin (4.8)

Reaction of 28 mg of 2 gave 10 mg 4.8 (31%). $R_f$($CHCl_3$/AcOEt/$CH_3OH$ 3:3:1) 0.48.

1,3,2',2''',6'''-Pentadeamino-1,3,2',2''',6'''-pentaazido-4, dichlorobenzylideneparomomycin (4.9)

Reaction of 80 mg of 2 gave 22 mg of 4.7 (23%). White solid. $R_f$($CHCl_3$/AcOEt/$CH_3OH$ 3:3:0.5) 0.39.

1,3,2',2''',6'''-Pentadeamino-1,3,2',2''',6'''-pentaazido-4',6'-O-p-cyanobenzylideneparomomycin (4.10)

Reaction of 115 mg of 2 gave 43 mg of 4.10 (33%). White solid. $R_f$ ($CHCl_3$/AcOEt/MeOH 3:3:0.5) 0.31. HR-Maldi-MS: 858.2722 (39, [M]$^+$, $C_{31}H_{38}N_{16}O_{14}^+$; calc. 858.2753); 857.2675 (100, [M–H]$^+$, $C_{31}H_{37}N_{16}O_{14}^+$; calc. 857.2681).

1,3,2',2''',6'''-Pentadeamino-1,3,2',2''',6'''-pentaazido-4',6'-O-p-phenylbenzylideneparomomycin (4.11)

Reaction of 80 mg of 2 gave 66 mg of 4.11 (68%). White solid. $R_f$($CHCl_3$/AcOEt/MeOH 3:3:0.5) 0.42. $[\alpha]_D^{29}$=+102.6 (c=0.29, $CH_3OH$). HR-Maldi-MS: 908.3058 (100, [M–H]$^+$, $C_{36}H_{42}N_{15}O_{14}^+$; calc. 908.3041); 909.3147 (40, [M]$^+$, $C_{36}H_{43}N_{15}O_{14}^+$; calc. 909.3114). Anal. calc. for $C_{36}H_{43}N_{15}O_{14}.CH_3OH$ (941.34): C, 47.18; H, 5.03; N, 22.31. found: C, 47.26, H, 5.11, N, 22.39.

1,3,2',2''',6'''-Pentadeamino-1,3,2',2''',6'''-pentaazido-4',6'-O-p-fluorobenzylideneparomomycin (4.12)

Reaction of 175 mg of 2 gave 139 mg of 4.12 (69%). White solid. $R_f$ ($CHCl_3$/AcOEt/MeOH 3:3:0.5) 0.34. HR-Maldi-MS: 890.2335 (28, [M+K]$^+$, $C_{30}H_{38}FKN_{15}O_{14}^+$; calc. 890.2344); 875.2620 (38, [M+Na+H]$^+$, $C_{30}H_{39}FN_{15}NaO_{14}^+$; calc. 875.2683); 874.2582 (100, [M+Na]$^+$, $C_{30}H_{38}FN_{15}NaO_{14}^+$; calc. 874.2599). Anal. calc. for $C_{30}H_{38}FN_{15}O_{14}.CH_3OH$ (883.7551): C, 42.13; H, 4.79; N, 23.77. found: C, 42.39; H, 4.79; N, 23.77.

Typical Procedure for the Deprotection of Azido Groups.

Under $N_2$, a soln. of 4.1-4.12 in THF was treated with 0.1 M aq. NaOH (2 equ.) and 1M $PMe_3$ in THF (6 equ.), stirred at 60°. Evaporation and FC (THF, THF/MeOH, MeOH, MeOH/25% aq. $NH_3$ 49:1→MeOH/25% aq. $NH_3$ 4:1) gave 5.1-5.12.

4',6'-O-benzylideneparomomycin (5.1)

Reaction of 110 mg of 4.1 gave 73 mg of 5.1 (79%). White solid. $R_f$ (MeOH/25% aq. $NH_3$ 4:1) 0.30. $[\alpha]_D^{25}$=+43.2 (c=0.25, $H_2O$). IR (ATR): 3355w, 3290w, 2909w, 1589w, 1455w, 1378w, 1334w, 1023s, 978s, 927m. $^1$H-NMR (500 MHz, $D_2O$, assignment based on DQF COSY and a HSQC spectrum): 7.57-7.55 (m, 2 arom. H); 7.50-7.48 (m, 3 arom.

H); 5.58 (s, PhCH); 5.55 (d, J=3.8, H—C(1')); 5.40 (d, J=2.3, H—C(1''')); 5.04 (d, J=1.7, H—C(1'''')); 4.44 (dd, J=6.6, 5.0, H—C(3'')); 4.35-4.31 (m, 2H, H—C(2''), F1, —C(6')); 4.18-4.13 (m, 2H, H—C(4''), H—C(5''')); 4.10-4.04 (m, 2H, H—C(3''), H—C(5')); 3.94-3.87 (m, 2H, $H_a$ C(5''), H—C(3')); 3.91 (t, J=10.5, $H_b$—C(6')); 3.77-3.73 (m, 2H, H—C(4'), H—C(5)); 3.74 (dd, J=10.0, 5.2, $H_b$—C(5'')); 3.71-3.70 (m, 1H, H—C(4''')); 3.54 (t, J=9.3, H—C(4)); 3.40 (t, J=9.7, H—C(6); 3.28 (dd, J=13.6, 7.9, $H_a$—C(6''')); 3.21 (dd, J=13.5, 3.9, $H_b$—C(6''')); 3.13 (m, 1H, H—C(2'')); 3.04-3.00 (m, 1H, H—C(3)); 2.99 (dd, J=10.0, 3.9, H—C(2')); 2.94-2.89 (m, 1H, H—C(1)); 2.07 (dt, J=13.0, 4.1, $H_{eq}$—C(2)); 1.34 (q, J=12.5, $H_{ax}$—C(2)). $^{13}$C-NMR (126 MHz, $D_2O$, assignment based on a HSQC spectrum): 138.79 (s); 132.61 (d), 131.43 (2d); 128.91 (2d); 111.35 (d, C(1'')); 104.52 (d, PhCH); 101.83 (d,C(1')); 101.18 (d, C(1''')); 86.96 (d, C(5)); 84.46 (d, C(4)); 83.89 (d, C(4'')); 83.52 (d, C(4')); 78.88 (d, C(6)); 78.06 (d, C(3'')); 76.05 (d, C(2'')); 74.61 (d, C(5'')); 72.73 (d, C(3''')); 72.56 (d, C(3'), 71.11 (d, C(4''')); 70.72 (t, C(6')); 66.32 (d, C(5')); 63.38 (t, C(5'')); 58.55 (d, C(2')); 54.87 (d, C(2''); 53.02 (d, C(1)); 52.24 (d, C(3)); 43.41 (t, C(6''')); 36.81 (t, C(2)). HR-Maldi-MS: 726.3117 (31, [M+Na]$^+$, $C_{30}H_{49}N_5NaO_{14}^+$; calc. 726.3174); 705.3347 (37, [M+2H]$^+$, $C_{30}H_{51}N_5O_{14}^+$; calc. 705.3433); 704.3336 (100, [M+H]$^+$, $C_{30}H_{50}N_5O_{14}^+$; calc. 704.3349). Anal. calc. for $C_{30}H_{49}N_5O_{14}$ (703.74): C, 51.20; H, 7.02; N, 9.95. found: C, 51.30; H, 7.15; N, 9.98.

4',6'-O-p-Methoxybenzylideneparomomycin (5.2)

Reaction of 17 mg of 4.2 gave 11 mg of 5.2 (76%). White solid.
$R_f$(MeOH/25% aq. $NH_3$ 4:1) 0.36. IR (ATR): 3355w (br.), 2917w, 1614w, 1518w, 1461w, 1378w, 1302w, 1250w, 1101s, 1024s, 937m. HR-Maldi-MS: 735.3475 (36, [M+2H]$^+$, $C_{31}H_{53}N_5O_{15}^+$; calc. 735.3538); 734.3442 (100, [M+H]$^+$, $C_{31}H_{52}N_5O_{15}^+$; calc. 734.3454).

4',6'-O-m-Methoxybenzylideneparomomycin tetraacetate (5.3)

Reaction of 26 mg of 4.3 gave 18 mg of 5.3 (81%). White solid. The product was converted into the tetraacetate salt by stirring in 20% aq. AcOH (23 mg). $R_f$(MeOH/25% aq. $NH_3$ 4:1) 0.34. IR (ATR): 3311w, 2884w, 1542m, 1402m, 1336w, 1285w, 1261w, 1096s, 1042s, 1014s. HR-Maldi-MS: 757.3323 (28, [M+Na+H]$^+$, $C_{31}H_{52}N_5NaO_{15}^+$; calc. 757.3358); 756.3287 (83, [M+Na]$^+$, $C_{31}H_{51}N_5NaO_{15}^+$; calc. 756.3279); 735.3468 (37, [M+2H]$^+$, $C_{31}H_{53}N_5O_{15}^+$; calc. 735.3538); 734.3442 (100, [M+H]$^+$, $C_{31}H_{52}N_5O_{15}^+$; calc. 734.3454); 574.2595 (31, [M–ring IV+2H]$^+$, $C_{25}H_{40}N_3O_{12}^+$; calc. 574.2612).

4,6'-O-o-Methoxybenzylideneparomomycin (5.4)

Reaction of 18 mg of 4.4 gave 21 mg of 5.4. White solid. $R_f$ (MeOH/25% aq. $NH_3$ 4:1) 0.31. $[\alpha]_D^{25}$=+51.3 (c=0.15, $H_2O$). IR (ATR): 3148w (br.), 1606w, 1526w, 1498w, 1463w, 1386w, 1287w, 1250w, 1095s, 1047s. HR-Maldi-MS: 757.3328 (25, [M+Na+H]$^+$, $C_{31}H_{52}N_5NaO_{15}^+$; calc. 757.3358); 756.3291 (67, [M+Na]$^+$, $C_{31}H_{51}N_5NaO_{15}^+$; calc. 756.3279); 735.3470 (36, [M+2H]$^+$, $C_{31}H_{53}N_5O_{15}^+$; calc. 735.3538); 734.3442 (100, [M+H]$^+$, $C_{31}H_{52}N_5O_{15}^+$; calc. 734.3454); 442.15.17 (32, [M–ring III–ring IV+2H]$^+$, $C_{20}H_{32}N_3O_8^+$; calc. 442.2189).

4',6'-O-2,5-Dimethoxybenzylideneparomomycin (5.5)

Reaction of 25 mg of 4.5 gave 21 mg of 5.5 (98%). White solid. $R_f$(MeOH/25% aq. $NH_3$ 4:1) 0.29. IR (ATR): 3287w, 2913w, 1593w, 1503m, 1464m, 1425w, 0.1386w, 1280w, 1221w, 1104s, 1019s. HR-Maldi-MS: 786.3382 (26, [M+Na]$^+$, $C_{32}H_{53}N_5NaO_{16}^+$; calc. 786.3385); 765.3571 (37, [M+2H]$^+$, $C_{32}H_{55}N_5O_{16}^+$; calc. 765.3644); 764.3545 (100, [M+H]$^+$, $C_{32}H_{54}N_5O_{16}^+$; calc. 764.3560).

4',6'-O-p-Nitrobenzylideneparomomycin (5.6)

Reaction of 14 mg of 4.6 gave 6 mg of 5.6 (50%). White solid. $R_f$(MeOH 25% aq. $NH_3$ 4:1) 0.24. $[\alpha]_D^{25}$=+168.1 (c=0.01, $H_2O$). IR (ATR): 3172w (br.), 2900w, 1611w, 1521w, 1349w, 1130s, 1099s, 995s. HR-Maldi-MS: 750.2943 (38, [M+2H]$^+$, $C_{30}H_{50}N_6O_{16}^+$; calc. 750.3283); 749.3196 (100, [M+H]$^+$, $C_{30}H_{49}N_6O_{16}^+$; calc. 749.3205).

4,6'-O-m-Nitrobenzylideneparomomycin triacetate (5.7)

Reaction of 16 mg of 4.7 gave after stirring in 10% aq. AcOH and evaporation 11 mg of 5.7 (61%): Yellowish solid. $R_f$(MeOH/25% aq. $NH_3$ 4:1) 0.31. IR (ATR): 3095m (br.), 1528m, 1406m, 1349m, 1100s, 1045s, 1014s, 937m. HR-Maldi-MS: 750.3211 (36, [M+2H]$^+$, $C_{30}H_{50}N_6O_{16}^+$; calc. 750.3283); 749.3187 (100, [M+H]$^+$, $C_{30}H_{49}N_6O_{16}^+$; calc. 749.3200).

4',6'-O-p-Chlorobenzylideneparomomycin (5.8)

Reaction of 17 mg of 4.8 gave 12 mg of 5.8 (83%). White solid. $R_f$(MeOH/25% aq. $NH_3$ 4:1) 0.36. IR (ATR): 3037w (br.), 1738w, 1603w 1524w, 1493w, 1454w, 1406w, 1375w, 1081s, 1049s, 1018s. HR-Maldi-MS: 738.2972 (95, [M+H]$^+$, $C_{30}H_{49}ClN_5O_{14}^+$; calc. 750.3283).

4,6'-O-3,5-Dichlorobenzylideneparomomycin (5.9)

Reaction of 25 mg of 4.9 gave 19 mg of 5.9 (89%). White solid. $R_f$(MeOH/25% aq. $NH_3$ 4:1) 0.29. IR (ATR): 3188w (br.), 2900w, 1597w, 1573w 1526w, 1429w, 1369w, 1101s, 1029s. HR-Maldi-MS: 772.2556 (100, [M+H]$^+$, $C_{30}H_{48}Cl_2N_5O_{14}^+$; calc. 772.2575).

4,6'-O-p-Cyanobenzylideneparomomycin (5.10)

Reaction of 10 mg of 4.10 gave 9 mg of 5.10. White solid. $R_f$(MeOH/25% aq. $NH_3$ 4:1) 0.27. IR (ATR): 3200w (br.), 1619w, 1526w, 1417w, 1094s, 996s. HR-Maldi-MS: 730.3322 (36, [M+2H]$^+$, $C_{31}H_{50}N_6O_{14}^+$; calc. 730.3385); 729.3288 (100, [M+H]$^+$, $C_{31}H_{49}N_6O_{14}^+$; calc. 729.3307).

4',6'-O-p-Phenylbenzylideneparomomycin (5.11)

Reaction of 20 mg of 4.11 gave 16 mg of 5.11 (93%). White solid. $R_f$ (MeOH/25% aq. $NH_3$ 4:1) 0.31. $[\alpha]_D^{25}$=+42.3 (c=0.14, $H_2O$). IR (ATR): 3356w, 3284w, 2903w, 1599w, 1532w, 1489w, 1451w, 1375w, 1110s, 1074s, 1026s. HR-Maldi-MS: 803.3565 (41, [M+Na+H]$^+$, $C_{36}H_{54}N_5NaO_{14}^+$; calc. 803.3565); 802.3462 (100, [M+Na]$^+$, $C_{36}H_{53}N_5NaO_{14}^+$; calc.) 802.3481); 780.3616 (48, [M+H]$^+$, $C_{36}H_{54}N_5O_{14}^+$; calc. 780.3667).

4,6'-O-p-Fluorobenzylideneparomomycin (5.12)

Reaction of 60 mg of 4.12 gave 51 mg of 5.11. White solid. $R_f$(MeOH/25% aq. $NH_3$ 4:1) 0.33. IR (ATR): 3285w, 2875w, 1606w, 1514w, 1457w, 1376w, 1300w, 1224w, 1047s, 1014s, 935m. $^1$H-NMR (500 MHz, D$_2$O, assignment based on DQF COSY and a HSQC spectrum): 7.54-7.50 (m, 2 arom. H); 7.19-7.13 (m, 2 arom. H); 5.71 (s, PhCH); 5.51 (d, J=3.9, H—C(1')); 5.35 (d, J=2.3, H—C(1")); 5.05 (d, J=1.8, H—C(1''')); 4.46 (dd, J=6.6, 4.9, H—C(3")); 4.32 (dd, J=4.9, 2.3, H—C(2")); 4.27 (dd, J=10.2, 4.8, H$_a$—C(6')); 4.18-4.11 (m, 2H, H—C(4"), H—C(5''')); 4.07 (t, J=3.2, H—C(3''')); 4.03-3.96 (m, H—C(5')); 3.88-3.82 (m, 3H, H$_a$—C(5"), H—C(3'), H$_b$—C(6')); 3.73-3.63 (m, 4H, H$_b$—C(5"), H—C(5), H—C(4'''), H—C(4')); 3.51 (t, J=9.4, H—C(4)); 3.44 (t, J=10.0, H—C(6); 3.32-3.21 (m, 2H, H$_a$—C(6"), H$_b$—C(6''')); 3.18 (t, J=1.8, H—C(2''')); 3.01 (dd, J=9.8, 3.9, H—C(2')); 3.00-2.93 (m, 2H, H—C(3), H—C(1)); 2.08 (dt, J=12.9, 4.1, H$_{aq}$—C(2)); 1.37 (q, J=12.5, H$_{ax}$—C(2)). $^{13}$C-NMR (126 MHz, D$_2$O, assignment based on a HSQC spectrum): 165.87 (d, $^1$J (C, F)=245.7); 135.04 (d, J=2.9, C$_{para}$); 131.09 (d, $^3$J (C, F)=8.7, 2 C$_{meta}$); 118.18 (d, $^2$J (C, F)=21.9, 2 C$_{ortho}$); 111.64 (d, C(1")); 103.83 (d, PhCH); 101.61 (d, C(1')); 100.55 (d, C(1''')); 86.95 (d, C(5)); 84.34 (d, C(4)); 83.91 (d, C(4")); 83.38 (d, C(4')); 78.06 (d, C(3")); 77.90 (d, C(6)); 76.02 (d, C(2")); 73.97 (d, C(5''')); 72.30 (d, C(3''')); 72.20 (d, C(3'), 70.90 (d, C(4''')); 70.67 (t, C(6')); 66.33 (d, C(5')); 63.37 (t, C(5")); 58.42 (d, C(2')); 54.61 (d, C(2''')); 53.12 (d, C(1)); 52.15 (d, C(3)); 43.35 (t, C(6''')); 35.95 (t, C(2)). HR-Maldi-MS: 744.3074 (32, [M+Na]$^+$, C$_{30}$H$_{48}$FN$_5$NaO$_{14}$$^+$; calc. 744: 3079); 723.3262 (34, [M+2H]$^+$, C$_{30}$H$_{50}$FN$_5$O$_{14}$$^+$; calc. 723.3338); 722.3242 (100, [M+H]$^+$, C$_{30}$H$_{49}$FN$_5$O$_{14}$$^+$; calc. 722.3255).

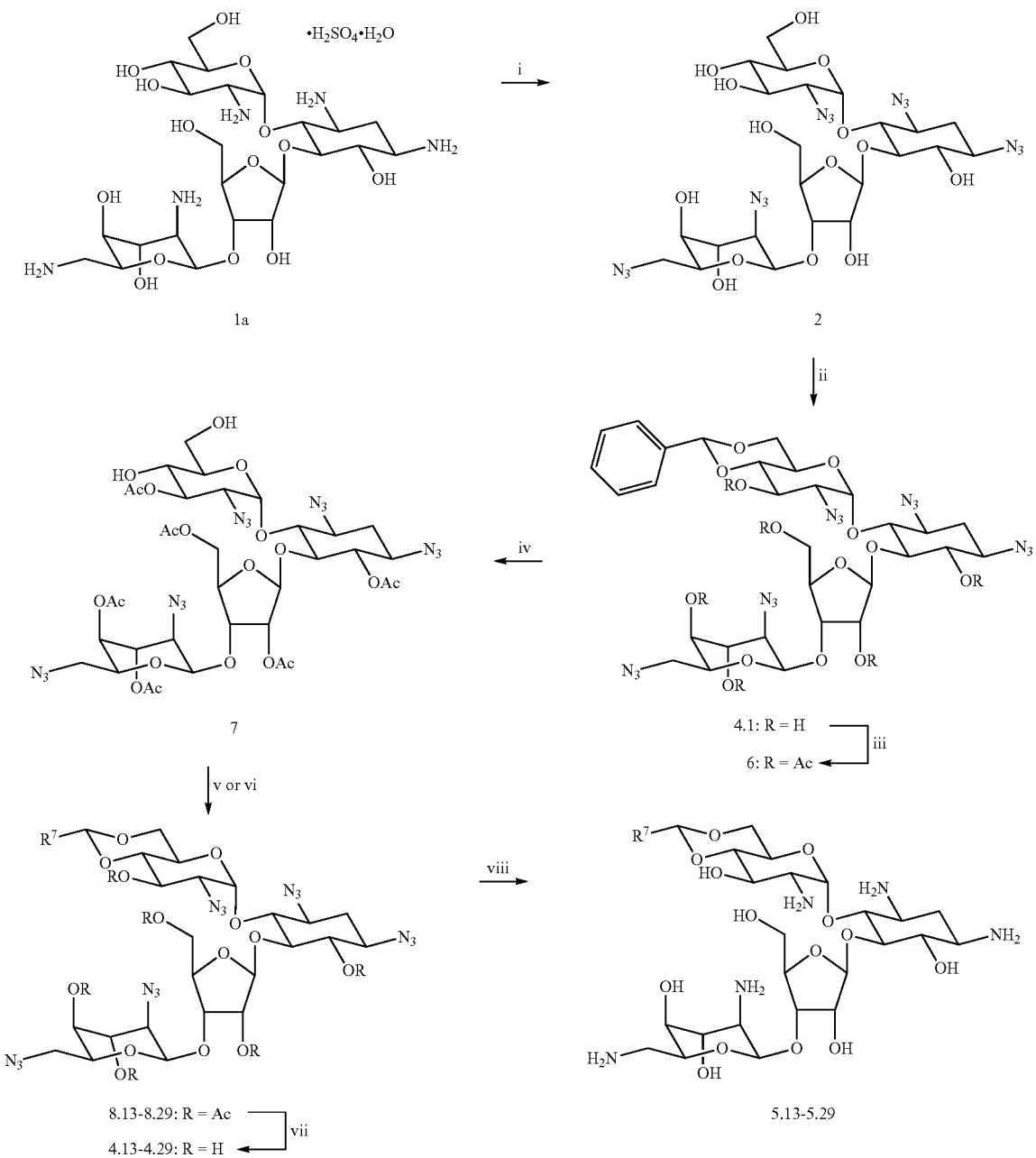

Scheme 2 i) TfN$_3$, CuSO$_4$, $^t$BuOK, H$_2$O/$^t$BuOH/CH$_2$Cl$_2$ 1/2/1, 23° C., 18h; ii) PhCHO, HCO$_2$H, -5°-0°, Ar, 24 h; iii) Ac$_2$O, DMAP, Pyr, Ar, 23°, 12 h, 42% from 1; iv) TsOH·H$_2$O, MeOH, 61%; v) R$^7$CHO, FeCl$_3$, N$_2$, 23°; vi) R$^7$CHO; TsOH·H$_2$O, toluene, N$_2$, reflux; vii) NaOMe, MeOH; viii) 0.1M aq. NaOH, 1M PMe$_3$ in THF, THF, N$_2$, 65°.

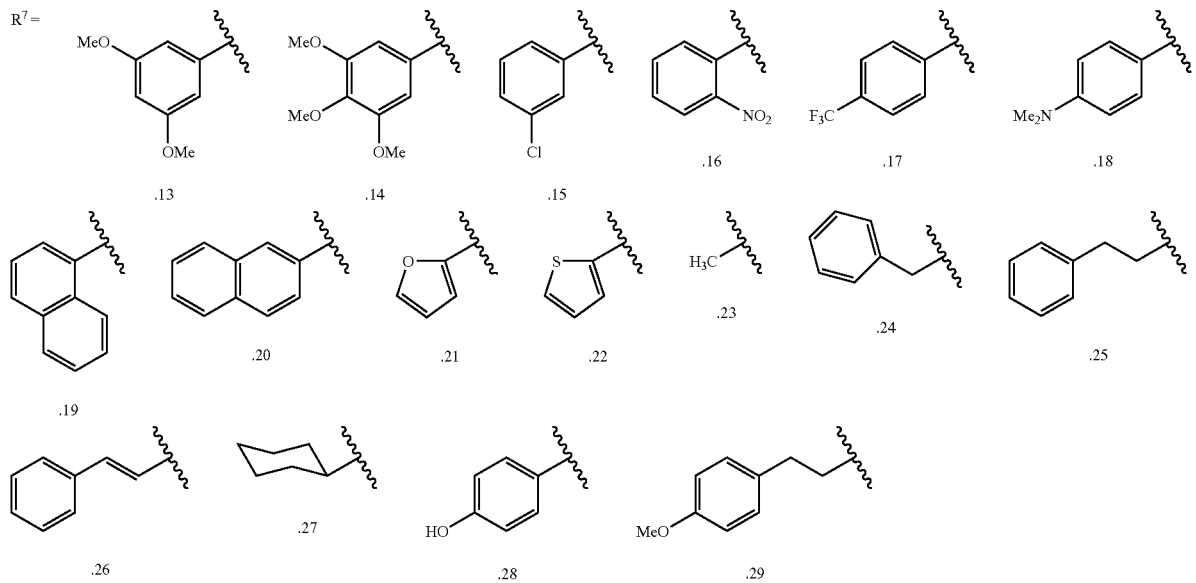

Compound 6 was synthesized as described in *Helv. Chim. Acta* 2005, 88, 2967.

6,3',2",5",3''',4'''-Hexa-O-acetyl-1,3,2',2''',6'''-pentadeamino-1,3,2',2''',6'''-pentaazido-paromomycin (7)

A soln. of 6 (23 mg, 0.021 mmol) in MeOH (1 ml) was treated with TsOH·H$_2$O (2 mg, 0.011 mmol), stirred at 25° for 5 h. The mixture was diluted with AcOEt (10 ml) and washed with H$_2$O (8 ml). The aq. Layer was extracted twice with AcOEt (2×10 ml). The combined org. layers were washed with brine (20 ml), dried (MgSO$_4$), filtered and evaporated. FC (Cyclohexane/AcOEt 8:2→cyclohexane/AcOEt 3:7 gave 7 (13 mg, 61%). White solid. R$_f$(CHCl$_3$/AcOEt/MeOH 3:3: 0.5) 0.57.

Typical Procedure for the Formation of the Acetals 4.13-4.27.

Method A:

Under N$_2$, a soln. of 7 in the aldehyde was treated with FeCl$_3$ and, stirred for 2-24 h at 23°. The mixture was diluted with AcOEt, filtered over Celite and washed with 0.1M aq. NaOH. The aqueous layer was extracted twice with AcOEt.

The combined org. layers were washed with brine, dried (MgSO$_4$), filtered, and evaporated. FC (Hexane or Cyclohexane/AcOEt 8:2→6:4) gave 8.15, 8.19, 8.21-8.27.

Method B:

Under N$_2$, a soln. of 7 in toluene was treated with 5 Å molecular sieves, TsOH·H$_2$O (0.5 equ.), a solution of the aldehyde (5 equ.) in toluene and, stirred for 2-24 h at reflux. The mixture was diluted with AcOEt, filtered over Celite and washed with 0.1M aq. NaOH: The aqueous layer was extracted twice with AcOEt. The combined org. layers were washed with brine, dried (MgSO$_4$), filtered, and evaporated. FC (Hexane or Cyclohexane/AcOEt 8:2→6:4) gave 8.13-8.14, 8.16-8.18, 8.20.)

6,3',2",5",3''',4'''-Hexa-O-acetyl-1,3,2',2''',6'''-pentadeamino-1,3,2',2''',6'''-pentaazido-4',6'-O-3,5-Dimethoxybenzylideneparomomycin (8.13)

Method B:

Reaction of 70 mg of 7 gave 58 mg of 8.13 (72%). White solid. R$_f$(Hexane/AcOEt 1:1) 0.34. HR-Maldi-MS (3-HPA): 1184.3294 (43, [M+K]$^+$, C$_{44}$H$_{55}$KN$_{15}$O$_{22}{}^+$; calc. 1184.3283); 1169.3562 (54, [M+Na+H]$^+$, C$_{44}$H$_{56}$N$_{15}$NaO$_{22}{}^+$; calc. 1169.3622); 1168.3568 (100, [M+Na]$^+$, C$_{44}$H$_{55}$N$_{15}$NaO$_{22}{}^+$; calc. 1168.3544).

6,3',2",5",3''',4'''-Hexa-O-acetyl-1,3,2',2''',6'''-pentadeamino-1,3,2',2''',6'''-pentaazido-4',6'-O-3,4,5-trimethoxybenzylideneparomomycin (8.14)

Method B:

Reaction of 61 mg of 7 gave 50 mg of 8.14 (70%). White solid. R$_f$(Hexane/AcOEt 1:1) 0.34. M.p. 95° (softens)-110°. [α]$_D{}^{25}$=+92.5 (c=0.23, CHCl$_3$). HR-Maldi-MS (3-HPA): 1215.3367 (31, [M+K+H]$^+$, C$_{45}$H$_{58}$KN$_{15}$O$_{23}{}^+$; calc. 1215.3467); 1214.3355 (57, [M+K]$^+$, C$_{45}$H$_{57}$KN$_{15}$O$_{23}{}^+$; calc. 1214.3389); 1199.3654 (56, [M+Na+H]$^+$, C$_{45}$H$_{58}$N$_{15}$NaO$_{23}{}^+$; calc. 1199.3728); 1198.3634 (100, [M+Na]$^+$, C$_{45}$H$_{57}$N$_{15}$NaO$_{23}{}^+$; calc. 1198.3649). Anal. calc. for C$_{45}$H$_{57}$N$_{15}$O$_{23}$ (1176.03): C, 45.96; H, 4.89; N, 17.87. found: C, 45.87; H, 5.03; N, 17.83.

6,3',2",5",3''',4'''-Hexa-O-acetyl-1,3,2',2''',6'''-pentadeamino-1,3,2',2''',6'''-pentaazido-4',6'-O-m-chlorobenzylideneparomomycin (8.15)

Method A:

Reaction of 153 mg of 7 gave 104 mg of 8.15 (61%). White solid. M.p. 76° (softens)-95°. R$_f$(Hexane/AcOEt 1:1) 0.60. [α]$_D{}^{25}$=+99.4 (c=0.20, CHCl$_3$). HR-Maldi-MS (3-HPA): 1158.2693 (35, [M+K]$^+$, C$_{42}$H$_{50}$ClKN$_{15}$O$_{20}{}^+$; calc. 111158.2682); 1144.2897 (44, [M+Na+2H]$^+$, C$_{42}$H$_{52}$ClN$_{15}$NaO$_{20}{}^+$; calc. 1144.3099); 1143.2983 (46, [M+Na+H]$^+$, C$_{42}$H$_{51}$ClN$_{15}$NaO$_{20}{}^+$; calc. 1143.3021); 1142.2934 (100, [M+Na]$^+$, C$_{42}$H$_{50}$ClN$_{15}$NaO$_{20}{}^+$; calc. 1142.2943).

6,3',2'',5'',3''',4''''-Hexa-O-acetyl-1,3,2',2''',6'''-pentadeamino-1,3,2',2''',6'''-pentaazido-4',6'-O-o-nitrobenzylideneparomomycin (8.16)

Method B:
Reaction of 91 mg of 7 gave 30 mg of 8.16 (29%).

6,3',2'',5'',3''',4''''-Hexa-O-acetyl-1,3,2',2''',6'''-pentadeamino-1,3,2',2''',6'''-pentaazido-4',6'-O-p-trifluoromethylbenzylideneparomomycin (8.17)

Method B:
Reaction of 89 mg of 7 gave 75 mg of 8.17 (73%). White solid. M.p. 71° (softens)-115°. $R_f$(Hexane/AcOEt 1:1) 0.58. M.p. 71-105°. $[\alpha]_D^{26}$=+98.2 (c=0.15, CHCl$_3$). HR-Maldi-MS (3-HPA): 1192.2894 (50, [M+K]$^+$, $C_{43}H_{50}F_3KN_{15}O_{20}^+$; calc. 1192.2946); 1177.3200 (52, [M+Na+H]$^+$, $C_{43}H_{51}F_3N_{15}NaO_{20}^+$; calc. 1177.3285); 1176.3182 (100, [M+Na]$^+$, $C_{43}H_{50}F_3N_{15}NaO_{20}^+$; calc. 1176.3201). Anal. calc. for $C_{43}H_{50}F_3N_{15}O_{20}\cdot0.5CH_3CO_2CH_2CH_3$ (1197.99): C, 45.12; H, 4.54; N, 17.54. found: C, 44.90, H, 4.63, N, 17.29.

6,3',2'',5'',3''',4''''-Hexa-O-acetyl-1,3,2',2''',6'''-pentadeamino-1,3,2',2''',6'''-pentaazido-4,6'-O-p-dimethylaminobenzylideneparomomycin (8.18)

Method B:
Reaction of 38 mg of 7 gave 75 mg of 8.18 (42%). Yellowish solid. $R_f$(Cyclohexane/AcOEt 1:1) 0.48. HR-Maldi-MS (3-HPA): 1168.3509 (48, [M+K+H]$^+$, $C_{44}H_{57}KN_{16}O_{20}^+$; calc. 1168.3572); 1167.3484 (86, [M+K]$^+$, $C_{44}H_{57}N_{16}O_{20}^+$; calc. 1167.3494); 1152.3798 (47, [M+Na+H]$^+$, $C_{44}H_{57}N_{16}NaO_{20}^+$; calc. 1152.3833); 1151.3769 (89, [M+Na]$^+$, $C_{44}H_{56}N_{16}NaO_{20}^+$; calc. 1151.3754); 1143.4066 (100, [M–CH$_3$+Na+7H]$^+$, $C_{43}H_{60}N_{16}NaO_{20}^+$; calc. 1143.4067); 1130.3905 (46, [M+2H]$^+$, $C_{44}H_{58}N_{16}O_{20}^+$; calc. 1130.4013); 1129.3858 (95, [M+H]$^+$, $C_{44}H_{57}N_{16}O_{20}^+$; calc.) 1129.3935).

6,3',2'',5'',3''',4''''-Hexa-O-acetyl-1,3,2',2''',6'''-pentadeamino-1,3,2',2''',6'''-pentaazido-4',6'-O-1-naphthylideneparomomycin (8.19)

Method A:
Reaction of 195 mg of 7 gave 157 mg of 8.19 (71%). White solid. $R_f$(Hexane/AcOEt 1:1) 0.55. M.p. 77° (softens)-115°. $[\alpha]_D^{25}$=+115.5 (c=0.21, CHCl$_3$). HR-Maldi-MS (3-HPA): 1175.3224 (46, [M+K+H]$^+$, $C_{46}H_{54}KN_{15}O_{20}^+$; calc. 1175.3307); 1174.3203 (82, [M+K]$^+$, $C_{46}H_{53}KN_{15}O_{20}^+$; calc. 1174.3228); 1159.3523 (56, [M+Na+H]$^+$, $C_{46}H_{54}N_{15}NaO_{20}^+$; calc. 1159.3567); 1158.3489 (100, [M+Na]$^+$, $C_{46}H_{53}N_{15}NaO_{20}^+$; calc. 1158.3489). Anal. calc. for $C_{46}H_{53}N_{15}O_{20}\cdot0.2CH_3CO_2CH_2CH_3$ (1153.62): C, 48.72; H, 4.77; N, 18.21. found: C, 48.76; H, 4.89; N, 17.77.

6,3',2'',5'',3''',4''''-Hexa-O-acetyl-1,3,2',2''',6'''-pentadeamino-1,3,2',2''',6'''-pentaazido-4',6'-O-2-naphthylideneparomomycin (8.20)

Method B:
Reaction of 80 mg of 7 gave 60 mg of 8.20 (66%). $R_f$ (Hexane/AcOEt 1:1) 0.64.

6,3',2'',5'',3''',4''''-Hexa-O-acetyl-1,3,2',2''',6'''-pentadeamino-1,3,2',2''',6'''-pentaazido-4,6'-O-2-furanylideneparomomycin (8.21)

Method A:
Reaction of 146 mg of 7 gave 91 mg of 8.21 (58%). Pale orange solid. $R_f$(Hexane/AcOEt 1:1) 0.60. M.p. 98° (softens)-105°. $[\alpha]_D^{25}$=+117.2 (c=0.11, CHCl$_3$). HR-Maldi-MS (3-HPA): 1115.2929 (40, [M+K+H]$^+$, $C_{40}H_{50}KN_{15}O_{21}^+$; calc. 1115.2943); 1114.2916 (75, [M+K]$^+$, $C_{40}H_{49}KN_{15}O_{21}^+$; calc. 1114.2865); 1099.3154 (50, [M+Na+H]$^+$, $C_{40}H_{50}N_{15}NaO_{21}^+$; calc. 1099.3203); 1098.3129 (100, [M+Na]$^+$, $C_{40}H_{43}N_{15}NaO_{21}^+$; calc. 1098.3125). Anal. calc. for $C_{40}H_{49}N_{15}O_{21}$ (1075.91): C, 44.65; H, 4.59; N, 19.53. found: C, 44.74; H, 4.59; N, 19.05.

6,3',2'',5'',3''',4''''-Hexa-O-acetyl-1,3,2',2''',6'''-pentadeamino-1,3,2',2''',6'''-pentaazido-4,6'-O-2-thiophenylideneparomomycin (8.22)

Method A:
Reaction of 80 mg of 7 gave 37 mg of 8.22 (42%). White solid. HR-Maldi-MS (3-HPA): 1130.2660 (52, [M+K]$^+$, $C_{40}H_{49}KN_{15}O_{20}S^+$; calc. 1130.2636); 1115.2904 (50, [M+Na+H]$^+$, $C_{40}H_{50}N_{15}NaO_{20}S^+$; calc. 1115.2975); 1114.2864 (100, [M+Na]$^+$, $C_{40}H_{49}N_{15}NaO_{20}S^+$; calc. 1114.2897). Anal. calc. for $C_{40}H_{49}N_{15}O_{20}S$ (1091.98): C, 44.00; H, 4.52; N, 19.24. found: C, 43.86; H, 4.61; N, 19.23.

6,3',2'',5'',3''',4''''-Hexa-O-acetyl-1,3,2',2''',6'''-pentadeamino-1,3,2',2''',6'''-pentaazido-4',6'-O-ethylideneparomomycin (8.23)

Method A:
Reaction of 21 mg of 7 gave 18 mg of 8.23 (84%). White solid. $R_f$(Hexane/AcOEt 1:1) 0.48. HR-Maldi-MS (3-HPA): 1047.3167 (46, [M+Na+H]$^+$, $C_{37}H_{50}N_{15}NaO_{20}^+$; calc. 1047.3254); 1046.3153 (100, [M+Na]$^+$, $C_{37}H_{49}N_{15}NaO_{20}^+$; calc. 1046.3176).

6,3',2'',5'',3''',4''''-Hexa-O-acetyl-1,3,2',2''',6'''-pentadeamino-1,3,2',2''',6'''-pentaazido-4',6'O-(2-phenyl)-ethylideneparomomycin (8.24)

Method A:
Reaction of 116 mg of 7 gave 97 mg of 8.24 (76%). White solid. M.p. 90° (softens)-96°. $R_f$(Hexane/AcOEt 1:1) 0.46. $[\alpha]_D^{25}$=+90.0 (c=0.105, CHCl$_3$). HR-Maldi-MS (3-HPA): 1138.3234 (39, [M+K]$^+$, $C_{43}H_{53}KN_{15}O_{20}^+$; calc. 1138.3228); 1123.3511 (53, [M+Na+H]$^+$, $C_{43}H_{54}N_{15}NaO_{20}^+$; calc. 1123.3567); 1122.3475 (100, [M+Na]$^+$, $C_{43}H_{53}N_{15}NaO_{20}^+$; calc. 1122.3489).

6,3',2'',5'',3''',4''''-Hexa-O-acetyl-1,3,2',2''',6'''-pentadeamino-1,3,2',2''',6'''-pentaazido-4',6'-O-(3-phenyl)-propylideneparomomycin (8.25)

Method A:
Reaction of 177 mg of 7 gave 189 mg of 8.25 (96%). White solid. $R_f$(Hexane/AcOEt 1:1) 0.50. M.p. 66° (softens)-86°. $[\alpha]_D^{25}$=+108.7 (c=0.24, CHCl$_3$). HR-Maldi-MS (3-HPA): 1153.3457 (27, [M+K+H]$^+$, $C_{44}H_{56}KN_{15}O_{20}^+$; calc. 1153.3463); 1152.3403 (49, [M+K]$^+$, $C_{44}H_{55}KN_{15}O_{20}^+$; calc. 1152.3385); 1137.3650 (54, [M+Na+H]$^+$, $C_{44}H_{56}N_{15}NaO_{20}^+$; calc. 1137.3724); 1136.3619 (100, [M+Na]$^+$, $C_{44}H_{55}N_{15}NaO_{20}^+$; calc. 1136.3640).

6,3',2'',5'',3''',4''''-Hexa-O-acetyl-1,3,2',2''',6'''-pentadeamino-1,3,2',2''',6'''-pentaazido-4',6'-O-(3-phenyl)-propenylideneparomomycin (8.26)

Method A:
Reaction of 75 mg of 7 gave 37 mg of 8.26 (44%).

6,3',2''',5'',3''',4''''-Hexa-O-acetyl-1,3,2',2''',6'''-pentadeamino-1,3,2',2''',6'''-pentaazido-4',6'-O-cyclohexylmethylideneparomomycin (8.27)

Method A:
Reaction of 157 mg of 7 gave 83 mg of 8.27 (49%). White solid.
Typical Procedure for the Formation of 4.13-4.27.
A soln. of 8.13-8.27 in $CH_2Cl_2$/MeOH ¼ was treated with NaOMe (12 equ.), stirred at 25°. The mixture was quenched with Amberlite IR-120($H^+$), filtered, and evaporated. FC($CHCl_3$/AcOEt 1:1→$CHCl_3$/AcOEt/MeOH) gave 4.13-4.27.

1,3,2',2''',6'''-Pentadeamino-1,3,2',2''',6'''-pentaazido-4',6'-O-3,5-dimethoxybenzylideneparomomycin (4.13)

Reaction of 19 mg of 8.13 gave 26 mg of 4.13 (98%). White solid. $R_f$($CHCl_3$/AcOEt/MeOH 3:3:0.5) 0.21.

1,3,2',2''',6'''-Pentadeamino-1,3,2',2''',6'''-pentaazido-4',6'-O-3,4,5-trimethoxybenzylideneparomomycin (4.14)

Reaction of 47 mg of 8.14 gave 30 mg of 4.13 (81%). White solid. $R_f$($CHCl_3$/AcOEt/MeOH 3:3:0.5) 0.22.

1,3,2',2''',6'''-Pentadeamino-1,3,2',2''',6'''-pentaazido-4',6'-O-m-chlorobenzylideneparomomycin (4.15)

Reaction of 70 mg of 8.15 gave 54 mg of 4.15 (quant.). White solid. $R_f$($CHCl_3$/AcOEt/MeOH 3:3:0.5) 0.45.

1,3,2',2''',6'''-Pentadeamino-1,3,2',2''',6'''-pentaazido-4',6'-O-o-nitrobenzylideneparomomycin (4.16)

Reaction of 54 mg of 8.16 gave 26 mg 4.16 (62%). White solid. $R_f$($CHCl_3$/AcOEt/MeOH 3:3:0.5) 0.51.

1,3,2',2''',6'''-Pentadeamino-1,3,2',2''',6'''-pentaazido-4',6'-O-p-trifluoromethylbenzylideneparomomycin (4.17)

Reaction of 57 mg of 8.17 gave 42 mg of 4.17 (94%). White solid. $R_f$($CHCl_3$/AcOEt/MeOH 3:3:0.5) 0.44. HR-Maldi-MS (3-HPA): 924.2549 (100, $[M+Na]^+$, $C_{31}H_{38}F_3N_{15}NaO_{14}^+$; calc. 924.2567).

1,3,2',2''',6'''-Pentadeamino-1,3,2',2''',6'''-pentaazido-4',6'-O-p-dimethylaminobenzylideneparomomycin (4.18)

Reaction of 39 mg of 8.18 gave 22 mg of 4.18 (73%). White solid. $R_f$($CHCl_3$/AcOEt/$CH_3$OH 3:3:0.5) 0.21.

1,3,2',2''',6'''-Pentadeamino-1,3,2',2''',6'''-pentaazido-4',6'-O-1-naphthylideneparomomycin (4.19)

Reaction of 107 mg of 8.19 gave 75 mg of 4.19 (90%). White solid. $R_f$($CHCl_3$/AcOEt/$CH_3$OH 3:3:0.5) 0.52.

1,3,2',2''',6'''-Pentadeamino-1,3,2',2''',6'''-pentaazido-4',6'-O-2-naphthylideneparomomycin (4.20)

Reaction of 60 mg of 8.20 gave 30 mg of 4.20 (65%). White solid. $R_f$ ($CHCl_3$/AcOEt/$CH_3$OH 3:3:0.5) 0.50. ESI-MS: 906.0 (100, $[M+Na]^+$, $C_{34}H_{41}N_{15}NaO_{14}^+$; calc. 906.3). Anal. calc. for $C_{34}H_{41}N_{15}O_{14}$ (883.79): C, 46.21; H, 4.68; N, 23.77. found: C, 46.44; H, 4.54; N, 23.37.

1,3,2',2''',6'''-Pentadeamino-1,3,2',2''',6'''-pentaazido-4,6'-O-2-furanylideneparomomycin (4.21)

Reaction of 73 mg of 8.21 gave 48 mg of 4.21 (86%). White solid. $R_f$($CHCl_3$/AcOEt/$CH_3$OH 3:3:0.5) 0.38.

1,3,2',2''',6'''-Pentadeamino-1,3,2',2''',6'''-pentaazido-4,6'-O-2-thiophenylideneparomomycin (4.22)

Reaction of 60 mg of 8.22 gave 37 mg of 4.22 (80%). White solid. $R_f$($CHCl_3$/AcOEt/$CH_3$OH 3:3:0.5) 0.40.

1,3,2',2''',6'''-Pentadeamino-1,3,2',2''',6'''-pentaazido-4',6'-O-ethylideneparomomycin (4.23)

Reaction of 29 mg of 8.23 gave 20 mg of 4.23 (92%). White solid. $R_f$($CHCl_3$/AcOEt/$CH_3$OH 3:3:0.5) 0.24.

1,3,2',2''',6'''-Pentadeamino-1,3,2',2''',6'''-pentaazido-4',6'-O-(2-phenyl)-ethylideneparomomycin (4.24)

Reaction of 79 mg of 8.24 gave 55 mg of 4.24 (90%). White solid. $R_f$($CHCl_3$/AcOEt/$CH_3$OH 3:3:0.5) 0.46.

1,3,2',2''',6'''-Pentadeamino-1,3,2',2''',6'''-pentaazido-4',6'-O-(3-phenyl)-propylideneparomomycin (4.25)

Reaction of 127 mg of 8.25 gave 75 mg of 4.25 (76%). White solid. $R_f$($CHCl_3$/AcOEt/$CH_3$OH 3:3:0.5) 0.45.

1,3,2',2''',6'''-Pentadeamino-1,3,2',2''',6'''-pentaazido-4',6'-O-(3-phenyl)-propenylideneparomomycin (4.26)

Reaction of 41 mg of 8.26 gave 24 mg of 4.26 (76%). White solid. $R_f$($CHCl_3$/AcOEt/$CH_3$OH 3:3:0.5) 0.48.

1,3,2',2''',6'''-Pentadeamino-1,3,2',2''',6'''-pentaazido-4',6'-O-cyclohexylmethylideneparomomycin (4.27)

Reaction of 46 mg of 8.27 gave 26 mg of 4.27 (74%). White solid. $R_f$($CHCl_3$/AcOEt/$CH_3$OH 3:3:0.5) 0.37.
Typical Procedure for the Final Deprotection.
Under $N_2$, a soln. of 4.13-4.27 in THF was treated with 0.1M aq. NaOH (2 equ.) and 1M $PMe_3$ in THF (6 equ.), stirred at 60°. Evaporation and FC (THF, THF/MeOH, MeOH, MeOH/25% aq. $NH_3$ 49:1→MeOH/25% aq. $NH_3$ 4:1) gave 5.13-5.27.

4',6'-O-3,5-Dimethoxybenzylideneparomomycin (5.13)

Reaction of 24 mg of 4.13 gave 19 mg of 5.13 (92%). White solid. $R_f$ (MeOH/25% aq. $NH_3$ 4:1) 0.34. IR (ATR): 3179w (br.), 2896w, 1597m, 1463w, 1431w, 1384w, 1338w, 1304w, 1200w, 1150s, 1087s, 1047s. HR-Maldi-MS: 765.3554 (36, $[M+2H]^+$, $C_{32}H_{55}N_5O_{16}^+$; calc. 765.3644); 764.3546 (100, $[M+H]^+$, $C_{32}H_{54}N_5O_{16}^+$; calc. 764.3560).

4',6'-O-3,4,5-Trimethoxybenzylideneparomomycin (5.14)

Reaction of 30 mg of 4.14 gave 21 mg of 5.14 (82%). White solid. $R_f$ (MeOH/25% aq. $NH_3$ 4:1) 0.19. IR (ATR): 3352w, 3289w, 3182w (br.), 2918w, 1593w, 1506w, 1462w, 1421w, 1380w, 1330w, 1236w, 1122s, 1026s, 994s.

HR-Maldi-MS: 795.3686 (40, [M+2H]$^+$, $C_{33}H_{57}N_5O_{17}^+$; calc. 795.3749); 794.3651 (100, [M+H]$^+$, $C_{33}H_{56}N_5O_{17}^+$; calc. 794.3651).

4',6'-O-m-chlorobenzylideneparomomycin (5.15)

Reaction of 52 mg of 4.15 gave 46 mg of 5.15. White solid. $R_f$(MeOH/25% aq. NH$_3$ 4:1) 0.33. HR-Maldi-MS: 740.2943 (43, [M+3H]$^+$, $C_{30}H_{51}ClN_5O_{14}^+$; calc. 740.3121); 739.2982 (38, [M+2H]$^+$, $C_{30}H_{50}ClN_5O_{14}^+$; calc. 739.3043); 738.2945 (100, [M+H]$^+$, $C_{30}H_{49}ClN_5O_{14}^+$; calc. 738.2959).

4',6'-O-o-Nitrobenzylideneparomomycin (5.16)

Reaction of 20 mg of 4.16 gave 17 mg of 5.16 (quant.). White solid. $R_f$ (MeOH/25% aq. NH$_3$ 4:1) 0.22. IR (ATR): 3179w (br.), 2895w, 1610w, 1528m, 1452w, 1349s, 1099s, 1048s, 1028s. HR-Maldi-MS: 771.2961 (31, [M+Na]$^+$, $C_{30}H_{48}N_6NaO_{16}^+$; calc. 771.3024); 750.3213 (46, [M+2H]$^+$, $C_{30}H_{50}N_6O_{16}^+$; calc. 750.3283); 749.3186 (100, [M+H]$^+$, $C_{30}H_{49}N_6O_{16}^+$; calc. 749.3205).

4',6'-O-p-Trifluoromethylbenzylideneparomomycin (5.17)

Reaction of 31 mg of 4.17 gave 26 mg of 5.17 (98%). White solid. $R_f$ (MeOH/25% aq. NH$_3$ 4:1) 0.32. IR (ATR): 3354w (br.), 2921w, 1583w, 1444w, 1378w, 1325s, 1122s, 1083s, 1066s, 1017s, 927m. HR-Maldi-MS: 773.3235 (36, [M+2H]$^+$, $C_{31}H_{50}F_3N_5O_{14}^+$; calc. 773.3306); 772.3210 (100, [M+H]$^+$, $C_{31}H_{49}F_3N_5O_{14}^+$; calc. 772.3223). $^{19}$F NMR: −60.85

4',6'-O-p-Dimethylaminobenzylideneparomomycin (5.18)

Reaction of 16 mg of 4.18 gave 13.5 mg of 5.18 (99%). White solid. $R_f$ (MeOH/25% aq. NH$_3$ 4:1) 0.27. IR (ATR): 3172w (br.), 2899w, 1615w, 1528w, 1454w, 1378w, 1360w, 1100s, 1048s, 996s. HR-Maldi-MS: 748.3811 (38, [M+2H]$^+$, $C_{32}H_{56}N_6O_{14}^+$; calc. 748.3855); 747.3774 (100, [M+H]$^+$, $C_{32}H_{55}N_6O_{14}^+$; calc. 747.3771).

4',6'-O-1-Naphthylideneparomomycin (5.19)

Reaction of 49 mg of 4.19 gave 39 mg of 5.19 (93%). White solid. $R_f$ (MeOH/25% aq. NH$_3$ 4:1) 0.32. IR (ATR): 3345w (br.), 2888w, 1599w, 1532w, 1509w, 1460w, 1392w, 1339w, 1272w, 1246w, 1104s, 1054s, 1028s, 996s, 972s, 920s. HR-Maldi-MS: 755.3519 (40, [M+2H]$^+$, $C_{34}H_{53}N_5O_{14}^+$; calc. 755.3589); 754.3495 (100, [M+H]$^+$, $C_{34}H_{52}N_5O_{14}^+$; calc. 754.3511).

4',6'-O-2-Naphthylideneparomomycin (5.20)

Reaction of 19 mg of 4.20 gave 12 mg of 5.20 (74%). White solid. $R_f$ (MeOH/25% aq. NH$_3$ 4:1) 0.36. IR (ATR): 3180w (br.), 2895w, 1600w, 1530w, 1467w, 1374w, 1346w, 1048s, 1026s HR-Maldi-MS: 776.3309 (56, [M+Na]$^+$, $C_{34}H_{51}N_5NaO_{14}^+$; calc. 776.3330); 755.3538 (36, [M+2H]$^+$, $C_{34}H_{53}N_5O_{14}^+$; calc. 755.3589); 754.3509 (100, [M+H]$^+$, $C_{34}H_{52}N_5O_{14}^+$; calc. 754.3511); 594.2633 (41, [M−ring IV+2H]$^+$, $C_{28}H_{40}N_3O_{11}^+$; calc. 594.2663); 462.2238 (63, [M−ring III−ring IV+2H]$^+$, $C_{23}H_{32}N_3O_7^+$; calc. 462.2240).

4',6'-O-2-Furanylideneparomomycin (5.21)

Reaction of 49 mg of 4.21 gave 39 mg of 5.21 (94%). White solid. $R_f$ (MeOH/25% aq. NH$_3$ 4:1) 0.21. IR (ATR): 3356w (br.), 2877w, 1664w, 1589w, 1506w, 1460w, 1460w, 1397w, 1359w, 1341w, 1135s, 1106s, 1026s, 994s, 918s. HR-Maldi-MS: 716.2997 (31, [M+Na]$^+$, $C_{28}H_{47}N_5NaO_{15}^+$; calc. 716.2966); 695.3146 (34, [M+2H]$^+$, $C_{28}H_{49}N_5O_{15}^+$; calc. 695.3225); 694.3128 (100, [M+H]$^+$, $C_{28}H_{48}N_5O_{15}^+$; calc. 694.3141).

4',6'-O-2-Thiophenylideneparomomycin (5.22)

Reaction of 42 mg of 4.22 gave 29 mg of 5.22 (82%). White solid. $R_f$ (MeOH/25% aq. NH$_3$ 4:1) 0.37. IR (ATR): 3353w, 3287w, 3174w (br.), 2909w, 1595w, 1543w, 1445w, 1377w, 1332w, 1243w, 1100s, 1053s, 1023s, 974s, 926s. HR-Maldi-MS: 733.2763 (33, [M+Na+H]$^+$, $C_{28}H_{48}N_5NaO_{14}S^+$; calc. 733.2816); 732.2730 (100, [M+Na]$^+$, $C_{28}H_{47}N_5NaO_{14}S^+$; calc. 732.2738).

4',6'-O-Ethylideneparomomycin (5.23)

Reaction of 18 mg of 4.23 gave 15 mg of 5.23 (99%). White solid. $R_f$ (MeOH/25% aq. NH$_3$ 4:1) 0.27. IR (ATR): 3286w (br.), 2888w, 1664w, 1571w, 1472w, 1392w, 1341w, 1102s, 1017s, 995s, 937w, 907w. HR-Maldi-MS: 665.3048 (31, [M+Na+H]$^+$, $C_{25}H_{48}N_5NaO_{14}^+$; calc. 665.3095); 664.3018 (100, [M+Na]$^+$, $C_{25}H_{47}N_5NaO_{14}^+$; calc. 664.3012).

4,6'-O-(2-Phenyl-ethylideneparomomycin (5.24)

Reaction of 52 mg of 4.24 gave 39 mg of 5.24 (89%). White solid. $R_f$ (MeOH/25% aq. NH$_3$ 4:1) 0.33. HR-Maldi-MS: 741.3349 (37, [M+Na+H]$^+$, $C_{31}H_{52}N_5NaO_{14}^+$; calc. 741.3408); 740.3312 (100, [M+Na]$^+$, $C_{31}H_{51}N_5NaO_{14}^+$; calc. 740.3330).

4',6'-O-(3-Phenyl)-propylideneparomomycin (5.25)

Reaction of 52 mg of 4.25 gave 35 mg of 5.25 (79%). White solid. $R_f$ (MeOH/25% aq. NH$_3$ 4:1) 0.27. IR (ATR): 3356w (br.), 2870w, 1740w, 1594w, 1495w, 1454w, 1386w, 1119s, 1016s, 931s. $^1$H-NMR (500 MHz, D$_2$O, assignment based on a HSQC spectrum): 7.40-7.37 (m, 2 arom. H); 7.33-7.27 (m, 3 arom. H); 5.47 (d, J=3.8, H—C(1')); 5.37 (d, J=2.5, H—C (1")); 5.00 (d, J=1.8, H—C(1'")); 4.68 (t, J=5.3, PhCH$_2$CH$_2$CH); 4.46 (dd, J=6.6, 5.0, H—C(3")); 4.31 (dd, J=4.9, 2.5, H—C(2")); 4.18-4.13 (m, 2H, H$_a$—C(6'), H—C (4")); 4.07-4.04 (m, 2H, H—C(5'"), H—C(3'")); 3.90-3.85 (m, 2H, H$_a$—C(5"), H—C(5')); 3.78-3.65 (m, 4H, H—C(3'), H—C(5), H$_b$—C(5"), H—C(4'")); 3.62 (t, J=10.5, H$_b$—C (6')); 3.47 (t, J=9.3, H—C(4)); 3.42 (t, J=9.6, H—C(4')); 3.40 (t, J=9.7, H—C(6); 3.17 (dd, J=13.5, 8.5, H$_a$—C(6")); 3.09-3.06 (m, 2H, H$_b$—C(6"), H—C(2'")); 2.93 (ddd, J=12.2, 9.5, 4.1, H—C(3)); 2.86 (dd, J=10.0, 3.8, H—C(2')); 2.82-2.75 (m, 2H, H—C(1), PhCH$_2$CH$_2$); 2.03-1.95 (m, 3H, H$_{eq}$—C (2), PhCH$_2$CH$_2$); 1.25 (q, J=12.4, H$_{ax}$—C(2)). HR-Maldi-MS: 755.3505 (38, [M+Na+H]$^+$, $C_{32}H_{54}N_5NaO_{14}^+$; calc. 755.3565); 754.3467 (100, [M+Na]$^+$, $C_{32}H_{53}N_5NaO_{14}^+$; calc. 754.3481); 732.3642 (38, [M+H]$^+$, $C_{32}H_{54}N_5O_{14}^+$; calc. 732.3667).

4',6'-O-(3-Phenyl)-propenylideneparomomycin (5.26)

Reaction of 24 mg of 4.26 gave 19 mg of 5.26 (92%). White solid. $R_f$ (MeOH/25% aq. NH$_3$ 4:1) 0.34. IR (ATR): 3353w, 3288w, 2915w, 1593w, 1493w, 1451w, 1377w, 1336w, 1135s, 1115s, 1054s, 1022s, 994s, 970s. HR-Maldi-MS: 731.3519 (37, [M+2H]$^+$, $C_{32}H_{53}N_5O_{14}^+$; calc. 731.3589); 730.3492 (100, [M+H]$^+$, $C_{32}H_{52}N_5O_{14}^+$; calc. 730.3511).

4',6'-O-Cyclohexylmethylideneparomomycin (5.27)

Reaction of 26 mg of 4.27 gave 16 mg of 5.27 (73%). White solid. $R_f$ (MeOH/25% aq. $NH_3$ 4:1) 0.25. IR (ATR): 3127m, 3029m, 2847w, 1753w, 1712w, 1613w, 1514w, 1441w, 1399m, 1101s, 996s. HR-Maldi-MS: 711.3859 (34, [M+2H]$^+$, $C_{30}H_{57}N_5O_{14}^+$; calc. 711.3902); 710.3822 (100, [M+H]$^+$, $C_{30}H_{56}N_5O_{14}^+$; calc. 710.3824).

Synthesis of 4'- and 6'-O-ether Derivatives

Scheme 3

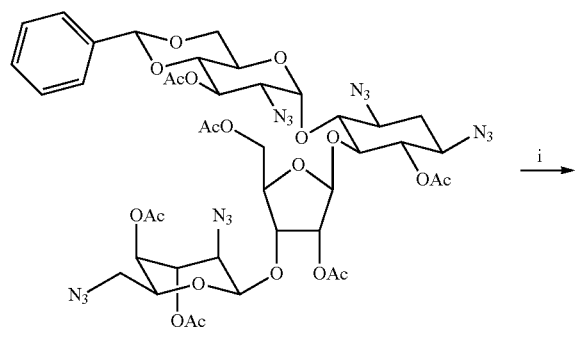

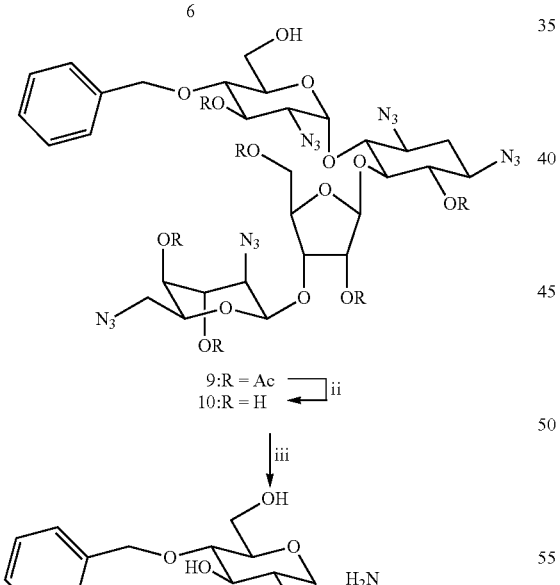

i) 2M $BH_3$·$Me_2S$ in THF, 1M $Bu_2BOTf$ in $CH_2Cl_2$, $CH_2Cl_2$, -5°, 61%;
ii) 0.02N MeONa, MeOH, 26°; 86%;
iii) 0.1M aq. NaOH, 1M $PMe_3$ in THF, THF, 50°; 79%.

6,3',2'',5'',3''',4'''-Hexa-O-acetyl-1,3,2',2''',6'''-pentadeamino-1,3,2',2''',6'''-pentaazido-4'-O-benzylparomomycin (9)

Under $N_2$, a soln. of 6 (1.8 g, 1.66 mmol) in dry $CH_2Cl_2$ (25 ml, dried over $CaH_2$) was cooled to −5° C., treated with 2M $BH_3$·$Me_2S$ in THF (8.3 ml, 16.6 mmol) and 1M $Bu_2BOTf$ in $CH_2Cl_2$ (0.83 ml, 0.83 mmol), and stirred for 5 h. After dilution with sat. $NaHCO_3$ soln. the layers were separated. The org. layer was washed with brine, dried ($MgSO_4$), filtered, and evaporated. FC (AcOEt/cyclohexane 9:11) gave 9 (1.1 g, 61%). $R_f$ (AcOEt/cyclohexane 1:1) 0.41. M.p. 82-86° C. $[\alpha]_D^{25}$=+98.2 (c=0.13, MeOH). IR (ATR): 2940w, 2872w, 2100s, 1740s, 1492w, 1453w, 1430w, 1371m, 1215s, 1027s. HR-ESI-MS: 1110.3489 (100, [M+Na]$^+$, $C_{42}H_{53}N_{15}NaO_{20}^+$; calc. 1110.3469). Anal. calc. for $C_{42}H_{53}N_{15}O_{20}$ (1087.97): C, 46.37; H, 4.91; N, 19.31, O 29.41. found: C, 46.27; H, 4.82; N, 19.02, O 29.38.

1,3,2',2''',6'''-Pentadeamino-1,3,2',2''',6'''-pentaazido-4'-O-benzylparomomycin (10)

Under $N_2$, a soln. of 9 (100 mg, 0.09 mmol) in 0.02N MeONa in MeOH (2 ml) was stirred at 26° C. for 12 h, and neutralized with Amberlite-IR 120 (H$^+$ form). Filtration, evaporation and FC ($CHCl_3$/AcOEt/MeOH 10:17.5:2) gave 10 (65 mg, 86%). White solid. $R_f$ ($CHCl_3$/AcOEt/MeOH 4:9:1) 0.45. M.p. 98° C. $[\alpha]_D^{25}$=+106.1 (c=0.14, MeOH). IR (KBr): 3418s, 2928m, 2107s, 1633m, 1497w, 1454m, 1384m, 1332m, 1261s, 1114m, 1068m, 1029s, 939w, 749w. HR-ESI-MS: 858.2835 (100, [M+Na]$^+$, $C_{30}H_{41}N_{15}NaO_{14}^+$; calc. 858.2855). Anal. calc. for $C_{30}H_{41}N_{15}O_{14}$·0.3AcOEt (862.17): C, 43.46; H, 5.07; N, 24.37. found: C, 43.13; H, 5.03; N, 24.47.

4'-O-Benzylparomomycin (11)

A soln. of 10 (30 mg, 0.04 mmol) in THF (3 ml) was treated with 0.1M aq. NaOH (1 ml) and 1M $PMe_3$ in THF. (0.22 ml, 0.22 mmol) and stirred at 50° C. for 2 h. Evaporation and FC (MeOH/25% aq. $NH_3$ 4:3) gave 11 (20 mg, 79%). White solid. $R_f$ ($CHCl_3$/MeOH/25% aq. $NH_3$ 1:3:4) 0.55. $[\alpha]_D^{25}$=+36.3 (c=0.11, $H_2O$). IR (KBr): 3418s, 2925m, 2852w, 1631m, 1537w, 1452w, 1397w, 1384m, 1298w, 1123s, 1051s, 947w. HR-ESI-MS: 728.3269 (100, [M+Na]$^+$, $C_{30}H_{51}N_5NaO_{14}^+$; calc. 728.3330); 706.3493 (100, [M+H]$^+$, $C_{30}H_{52}N_5O_{14}^+$; calc. 706.3511).

Scheme 4

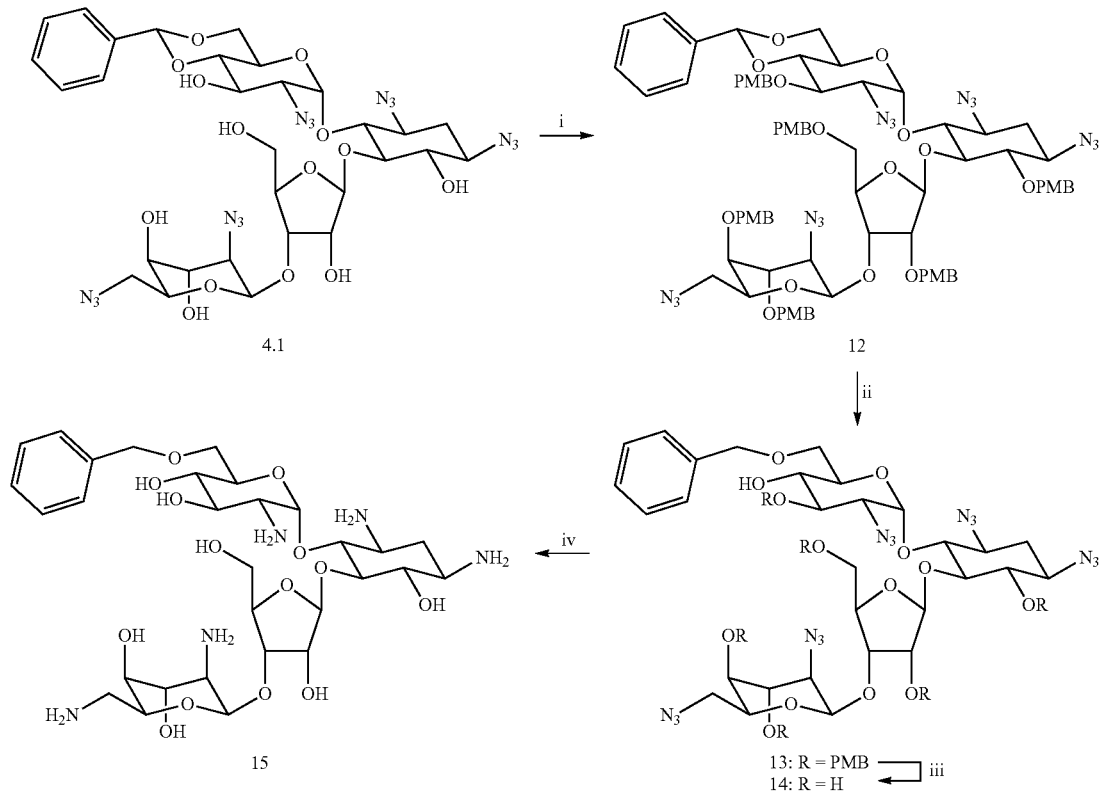

i) NaH, p-MeOBnCl, Bu₄NI, THF, 0-26°, 48%; ii) NaCNBH₃, 0.7M HCl in Et₂O, 4 Å MS, THF, 0°, 33%; iii) DDQ, CH₂Cl₂/H₂O/i-PrOH 20:1:1, 0-26°, 59%; iv) 0.1M aq. NaOH, 1M PMe₃ in THF, THF, 50°, 85%.

1,3,2',2''',6'''-Pentadeamino-1,3,2',2''',6'''-pentaazido-4',6'-O-benzylidene-6,3',2'',5'',3''',4'''-hexakis-O-(4-methoxybenzyl)paromomycin (12)

Under Ar, a soln. of 4.1 (810 mg, 0.97 mmol) in THF (20 ml) was treated with NaH (637 mg, 50-60% suspension in oil, ca 13.3 mmol), p-MeOBnCl (0.90 ml, 6.66 mmol), and Bu₄NI (110 mg), stirred at 0° C. for 4 h and at 26° C. for 20 h, cooled to 0° C., and diluted portionwise with H₂O. After evaporation, the aq. layer was extracted with AcOEt (3×20 ml). The combined org. layers were washed with brine, dried (MgSO₄), filtered, and evaporated. FC (AcOEt/cyclohexane 1:4) gave 12 (722 mg, 48%). White solid. $R_f$ (AcOEt/cyclohexane 1:1) 0.46. M.p. 54.6-56.4° C. (softens at 46° C.). $[\alpha]_D^{25}=+75.8$ (c=0.40, CHCl₃). IR (CHCl₃): 3021w, 3006w, 2937w, 2839w, 2867w, 2106s, 1612m, 1586w, 1514s, 1465w, 1442w, 1368w, 1302w, 1250s, 1174m, 1091m, 1035m, 847w, 823w. HR-ESI-MS: (100, [M+Na]⁺, $C_{78}H_{87}N_{15}NaO_{20}^+$; calc. 1576.6149). Anal. calc. for $C_{78}H_{87}N_{15}O_{20}$ (1554.61): C, 60.26; H, 5.64; N, 13.51. found: C, 60.23, H, 5.81, N, 13.31.

1,3,2',2''',6'''-Pentadeamino-1,3,2',2''',6'''-pentaazido-6'-O-benzyl-6,3',2'',5'',3''',4'''-hexakis-O-(4-methoxybenzyl)paromomycin (13)

Under N₂, a soln. of 12 (677 mg, 0.44 mmol) in THF (15 ml) was treated with 4 Å molecular sieves, stirred for 1 h, cooled to 0° C., treated with NaCNBH₃ (443 mg, 7.05 mmol) at 0° C., and then dropwise within 1 h with 0.7M HCl in Et₂O (14 ml, 9.80 mmol) (methyl orange was added to indicate the pH of solution) and stirred for 4 h. After neutralization with sat. NaHCO₃ soln. and evaporation, the aq. layer was extracted with AcOEt (3×25 ml). The combined org. layers were washed with brine, dried (MgSO₄), filtered, and evaporated. FC (AcOEt/cyclohexane 3:7) gave 13 (219 mg, 33%). White solid. $R_f$ (AcOEt/cyclohexane 1:1) 0.42. M.p. 52-55° C. $[\alpha]_D^{25}=+66.9$ (c=0.37, CHCl₃). IR (CHCl₃): 3673w, 3020s, 2937w, 2839w, 2106s, 1612m, 1583w, 1514m, 1465w, 1438w, 1366w, 1302w, 1250m, 1174w, 1118w, 1072w, 1035m, 901w. HR-ESI-MS: 1578.6274 (100, [M+Na]⁺, $C_{78}H_{89}N_{15}NaO_{20}^+$; calc. 1578.6306); 1529.6556 (84, [M−N₂+2H]⁺, $C_{78}H_{91}N_{13}NaO_{20}^+$; calc. 1529.6503); 1528.6536 (94, [M−N₂+H]⁺, $C_{78}H_{90}N_{13}NaO_{20}^+$; calc. 1528.6425). Anal. calc. for $C_{78}H_{89}N_{15}O_{20}$ (1556.65): C, 60.18; H, 5.76; N, 13.50. found: C, 60.05; H, 5.64; N, 13.47.

1,3,2',2''',6'''-Pentadeamino-1,3,2',2''',6'''-pentaazido-6'-O-benzylparomomycin (14)

Under N₂, a soln. of 13 (107 mg, 0.07 mmol) in CH₂Cl₂/H₂O/i-PrOH 20:1:1 (7 ml) was treated with DDQ (103 mg, 0.45 mmol) at 0° C. and stirred for 2 h and at 26° C. for 24 h. The colour of the mixture changed from colourless to green and then to light orange. After neutralization with sat. NaHCO₃ soln., the aq. layer was extracted with AcOEt (3×20 ml). The combined org. layers were washed with brine, dried (MgSO₄), filtered, and evaporated. FC (CHCl₃/AcOEt/MeOH 10:17.5:2)) gave 14 (34 mg, 59%). White solid. $R_f$ (CHCl$_3$/AcOEt/MeOH 4:9:1) 0.68. M.p. 89.1-92.9° C. [α]$_D^{25}$=+97.2 (c=0.12, MeOH). IR (KBr): 3434s, 2929w, 2107s, 1635w, 1500w, 1401w, 1384m, 1331w, 1262m, 1140m, 1077m, 1036m, 743w. HR-ESI-MS: 858.2836 (100, [M+Na]$^+$, C$_{30}$H$_{41}$N$_{15}$NaO$_{14}^+$; calc. 858.2855). Anal. calc. for C$_{30}$H$_{41}$N$_{15}$O$_{14}$·CH$_3$OH (867.78): C, 42.91; H, 5.23; N, 24.21. found: C, 42.73; H, 4.96; N, 24.25.

6'-O-Benzylparomomycin (15)

A soln. of 14 (25 mg, 0.03 mmol) in THF (3 ml) was treated with 0.1M aq. NaOH (1 ml) and 1M PMe$_3$ in THF (0.22 ml, 0.22 mmol) and heated to 50° C. for 2 h. Evaporation and FC (MeOH/25% aq. NH$_3$ 4:3) gave 15 (18 mg, 85%). White solid. R$_f$(CHCl$_3$/MeOH/25% aq. NH$_3$ 1:4:3) 0.56. M.p. 165° C. (dec.). [α]$_D^{25}$=+28.1 (c=0.08, H$_2$O). IR (KBr): 3420s, 2925m, 1633m, 1595m, 1491w, 1454w, 1397w, 1384m, 1252w, 1151m, 1092m, 1026s, 1051s, 741w. HR-ESI-MS: 728.3269 (100, [M+Na]$^+$, C$_{30}$H$_{51}$N$_5$NaO$_{14}^+$; calc. 728.3330); 706.3493 (100, [M+H]$^+$, C$_{30}$H$_{52}$N$_5$O$_{14}^+$; calc. 706.3511). Anal. calc. for C$_{30}$H$_{51}$N$_5$O$_{14}$·6 AcOH·3H$_2$O (1120.11)$^±$: C, 45.04; H, 7.29; N, 6.25. found: C, 44.85; H, 6.72; N, 6.68.

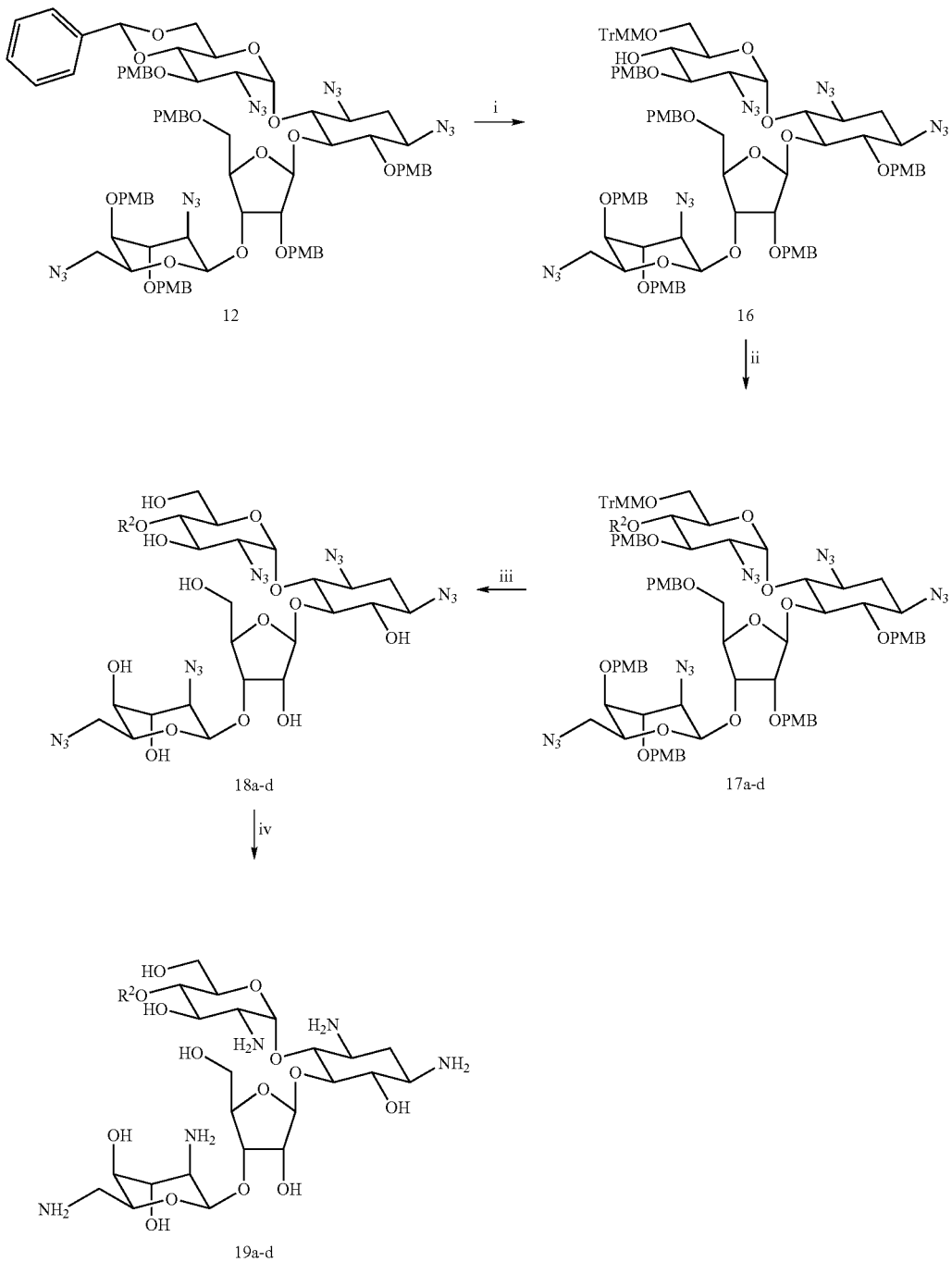

Scheme 5

R² = 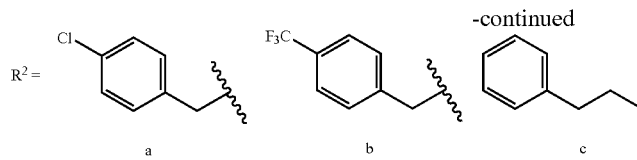 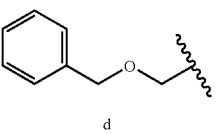

a      b      c      d i) a) TsOH·H$_2$O, CH$_2$Cl$_2$, CH$_3$OH, N$_2$, 25°, 79%; b) MMTrCl, NaH, DMF, N$_2$, 25°, 65%;
ii) R²Cl, NaH, DMF, N$_2$, 25°; iii) DDQ, CH$_2$Cl$_2$/H$_2$O/MeOH 20:1:0.4, 25°; iv) 0.1M aq. NaOH, 1M PMe$_3$ in THF, THF, N$_2$, 65°.

Typical Procedure for the Formation of Ethers 16,17a-d (Scheme 5). (GP 1):

Under N$_2$, a soln. of alcohol (1 equ.) in DMF (c=0.1) was treated with NaH (1.5 equ. per hydroxyl group, 50-60% suspension in oil), followed by alkyl chloride (or bromide) (1.5 equ. per hydroxyl group) and Bu$_4$NI (0.1 equ.), stirred at 25° C. for 4-24 h, and diluted with H$_2$O and Et$_2$O. After separation of phases, the aq. layer was extracted with Et$_2$O (3×). The combined org. layers were dried (MgSO$_4$) and evaporated. FC.

1,3,2',2''',6'''-Pentadeamino-1,3,2',2''',6'''-pentaazido-6,3',2'',5'',3''',4'''-hexa-O-p-methoxybenzyl-4'-hydroxy-6'-O-monomethoxytritylparomomycin (16)

Under N$_2$, a soln. of 12 (400 mg, 0.256 mmol) in MeOH/CH$_2$Cl$_2$ (10:1, 5.5 ml) was treated with TsOH.H$_2$O (49 mg, 0.3 mmol), stirred at 25° C. for 3 h, and diluted with 1N NaOH. After separation of phases, the aq. layer was extracted with CH$_2$Cl$_2$ (3×5 ml). The combined org. layers were dried (MgSO$_4$) and evaporated. FC gave as a white solid 1,3,2',2''',6'''-Pentadeamino-1,3,2',2''',6'''-pentaazido-6',4'-dihydroxy-6,3',2'',5'',3''',4'''-hexa-O-p-methoxybenzyl paromomycin (296 mg, 79%), R$_f$(AcOEt/cyclohexane 1:1) 0.37, which was reacted according to GP 1. Reaction gave 16 (1.319 mg, 65%). R$_f$ (AcOEt/cyclohexane 3:7) 0.58. White solid, m.p. 60-65° C. $[\alpha]_D^{25}$=+96.4 (c=0.12, CHCl$_3$). IR (ATR): 2927w, 2103s, 1611m, 1581w, 1513w, 1460w, 1362w, 1303w, 1249s, 1173m, 1033s. HR-Maldi-MS: 1776.6813 (92, [M+K]$^+$, C$_{91}$H$_{99}$N$_{15}$KO$_{21}^+$; calc. 1776.6777); 1760.7034 (82, [M+Na]$^+$, C$_{91}$H$_{99}$N$_{15}$NaO$_{21}^+$; calc. 1760.7038). Anal. calc. for C$_{91}$H$_{99}$N$_{15}$O$_{21}$ (1738.85): C, 62.86; H, 5.74; N, 12.08. found: C, 63.25; H, 6.06; N, 11.55.

1,3,2',2''',6'''-Pentadeamino-1,3,2',2''',6'''-pentaazido-6,3',2'',5'',3''',4'''-hexa-O-p-methoxybenzyl-4'-O-p-chlorobenzyl-6'-O-monomethoxytritylparomomycin (17a)

(GP 1) Reaction of 16 gave 17a (518 mg, 96%). R$_f$(AcOEt/cyclohexane 3:7) 0.54. White solid, m.p. 66-71° C. $[\alpha]_D^{25}$=+94.1 (c=0.08, ChCl3). IR (atr): 2932w, 2099s, 1611m, 1585w, 1512s, 1462w, 1359w, 1301w, 1245s, 1173m, 1110m, 1068m, 1031s. HRMaldi-MS: 1900.6892 (57, [M+K]$^+$, C$_{98}$H$_{104}$ClN$_{15}$KO$_{21}^+$; calc. 1900.6857); 1884.7151 (84, [M+Na]$^+$, C$_{98}$H$_{104}$N$_{15}$ClNaO$_{21}^+$; calc. 1884.7117). Anal. calc. for C$_{100}$H$_{109}$N$_{15}$O$_{21}$.1.5H$_2$O (1890.44): C, 62.26; H, 5.71; N, 11.11. found: C, 62.39, H, 5.83, N, 10.73.

1,3,2',2''',6'''-Pentadeamino-1,3,2',2''',6'''-pentaazido-6,3',2'',5'',3''',4'''-hexa-O-p-methoxybenzyl-4'-O-p-(trifluoromethyl)benzyl-6'-O-monomethoxytritylparomomycin (17b). (GP 1)

Reaction of 16 gave 17b (441 mg, 85%). R$_f$(AcOEt/cyclohexane 3:7×2) 0.54. White solid, m.p. 60-76° C. $[\alpha]_D^{25}$= +70.3) (c=0.26, ChCl3). Ir (ATR): 2934w, 2100s, 1611m, 1586w, 1512s, 1463w, 1362w, 1325m, 1302m, 1245s, 1173m, 1111m, 1065s, 1030s. HR-Maldi-MS: 1934.7083 (84, [M+K]$^+$, C$_{99}$H$_{104}$F$_3$N$_{15}$KO$_{21}^+$; calc. 1934.7120); 1918.7333 (80, [M+Na]$^+$, C$_{99}$H$_{104}$N$_{15}$F$_3$NaO$_{21}^+$; calc. 1918.7381). Anal. calc. for C$_{99}$H$_{104}$N$_{15}$O$_{21}$F$_3$ (1896.97): C, 62.68, H, 5.53, N, 11.08. found: C, 62.42; H, 5.62; N, 10.66.

1,3,2',2''',6'''-Pentadeamino-1,3,2',2''',6'''-pentaazido-6,3',2'',5'',3''',4'''-hexa-O-p-methoxybenzyl-4'-O-propylphenyl-6'-O-monomethoxytritylparomomycin (17c). (GP 1)

Reaction of 16 gave 17c (459 mg, 86%). R$_f$(AcOEt/cyclohexane 3:7) 0.6. White solid, m.p. 63-78° C. $[\alpha]_D^{25}$=+56.9 (c=0.65, CHCl$_3$). IR (ATR): 2933w, 2099s, 1672w, 1611m, 1585w, 1512s, 1454w, 1363w, 1301w, 1245s, 1174m, 1029s. HR-Maldi-MS: 1894.7513 (72, [M+K]$^+$, C$_{100}$H$_{109}$N$_{15}$KO$_{21}^+$; calc. 1894.7560); 1878.7773 (82, [M+Na]$^+$, C$_{91}$H$_{99}$N$_{15}$NaO$_{21}^+$; calc. 1878.7820). Anal. calc. for C$_{100}$H$_{109}$N$_{15}$O$_{21}$ (1857.02): C, 64.68; H, 5.92; N, 11.31. found: C, 65.08; H, 5.71; N, 10.86.

1,3,2',2''',6'''-Pentadeamino-1,3,2',2''',6'''-pentaazido-6,3',2'',5'',3''',4'''-hexa-O-p-methoxybenzyl-4'-O-benzyloxymethyl-6'-O-monomethoxytritylparomomycin (17d). (GP 1)

Reaction of 16 gave 17d (442 mg, 83%). R$_f$(AcOEt/cyclohexane 3:7) 0.54. White solid, m.p. 52-55° C. IR (ATR): 2933w, 2001s, 1611m, 1585w, 1513w, 1463w, 1361w, 1301m, 1247s, 1174m, 1111m, 1068m, 1033s. HR-Maldi-MS: 1896.7326 (16, [M+Na]$^+$, C$_{99}$H$_{107}$N$_{15}$KO$_{22}^+$; calc. 1896.7352); 1880.7566 (22, [M+Na]$^+$, C$_{99}$H$_{107}$N$_{15}$NaO$_{22}^+$; calc. 1880.7613); 1866.7181 (65, [M–CH$_3$O+K]$^+$, C$_{98}$H$_{105}$N$_{15}$KO$_{21}^+$; calc. 1866.7247); 1850.7403 (89, [M—CH$_3$O+Na]$^+$, C$_{98}$H$_{105}$N$_{15}$NaO$_{21}^+$; calc. 1850.7507).

General Procedure for Deprotection of Protected Derivatives to Give Compounds 19a-d: (GP 2):

Under N$_2$, a soln. of protected derivative 17 (1 equiv.) in CH$_2$Cl$_2$/MeOH/H$_2$O 20:1:0.4 (c=0.02) was treated with DDQ (1.1 equiv. per group), stirred at 25° C. for 12-24 h, and neutralized with 1N NaOH, diluted with AcOEt. After separation of phases, the aq. layer was extracted with AcOEt (3×). The combined org. layers were dried (MgSO$_4$) and evaporated. FC. A soln. of azido compound (1 equiv.) in THF/0.1M NaOH 4:1 (c=0.03) was treated with 1M PMe$_3$ in THF (1.2 equiv. per azido group) and stirred for 4-8 h at 50° C. After evaporation, FC.

4'-p-chlorobenzylparomomycin (19a). (GP 2)

Reaction of 17a gave azido intermediate 18a (120 mg, 54%) as a white solid. R$_f$ (MeOH/CHCl$_3$/AcOEt 0.5:2:2) 0.29. Final compound 19a (47 mg, 86%). R$_f$(MeOH/NH$_{3aq}$ 8:2) 0.27. White solid, m.p. 145° C. (decomp.). $[\alpha]_D^{27}$=+60.3

(c=0.27, H$_2$O). IR (atr): 3358m, 2915m, 1590w, 1454w, 1366w, 1088s, 1014s. HR-Maldi-MS: 762.2921 (100, [M+Na]$^+$, C$_{30}$H$_{50}$ClN$_5$NaO$_{14}$$^+$; calc. 762.2940); 740.3110 (86, [M+H]$^+$, C$_{30}$H$_{51}$ClN$_5$O$_{14}$$^+$; calc. 740.3121).

4'-p-(trifluoromethyl)benzylparomomycin (19b). (GP 2)

Reaction of 17b gave azido intermediate 18b (130 mg, 80%) as a white solid. R$_f$ (MeOH/CHCl$_3$/AcOEt 0.5:2:2) 0.26. Final compound 19b (84 mg, 87%). R$_f$ (MeOH/NH$_{3aq}$. 8:2) 0.30. White solid, m.p. 148° C. (dec.). [α]$_D^{25}$=+65.4 (c=0.16, H$_2$O). IR (ATR): 3156m, 2921m, 1551m, 1403m, 1326s, 1107s, 1064s, 1016s. HR-Maldi-MS: 796.3201 (72, [M+Na]$^+$, C$_{31}$H$_{50}$F$_3$N$_5$NaO$_{14}$$^+$; calc. 796.3204); 774.3366 (100, [M+H]$^+$, C$_{31}$H$_{51}$F$_3$N$_5$O$_{14}$$^+$; calc. 774.3385).

4'-p-(3-phenylpropyl)paromomycin (19c). (GP 2)

Reaction of 17c gave azido intermediate 18c (105 mg, 74%) as a white solid. R$_f$ (MeOH/CHCl$_3$/AcOEt 0.5:2:2) 0.40. Final compound 19c (64 mg, 92%). R$_f$ (CHCl$_3$/MeOH/NH$_{3aq}$. 1:3:2) 0.47. White solid, m.p. 179° C. (dec.). [α]$_D^{25}$=+63.0 (c=0.12, H$_2$O). IR (ATR): 3191w, 2920w, 1572w, 1495w, 1454w, 1381w, 1339w, 1015s. HR-Maldi-MS: 756.3648 (37, [M+Na]$^+$, C$_{32}$H$_{55}$N$_5$NaO$_{14}$$^+$; calc. 756.3643); 734.3805 (100, [M+H]$^+$, C$_{32}$H$_{56}$N$_5$O$_{14}$$^+$; calc. 734.3824).

4'-Benzyloxymethylparomomycin (19d). (GP 2)

Reaction of 17d gave azido intermediate 18d (70 mg, 72%) as a white solid. R$_f$ (MeOH/CHCl$_3$/AcOEt 0.5:2:2) 0.31. Final compound 19d (36 mg, 72%). R$_f$ (CHCl$_3$/MeOH/NH$_{3aq}$. 1:3:2) 0.36. White solid, m.p. 143° C. (decomp.). [α]$_D^{27}$=+48.9 (c=0.24, H$_2$O). IR (ATR): 3031m, 1622w, 1525w, 1429m, 1043s. HR-Maldi-MS: 758.3428 (20, [M+Na]$^+$, C$_{31}$H$_{53}$N$_5$NaO$_{15}$$^+$; calc. 758.3436); 736.3598 (100, [M+H]$^+$, C$_{31}$H$_{54}$N$_5$O$_{15}$$^+$; calc. 736.3616).

Scheme 6

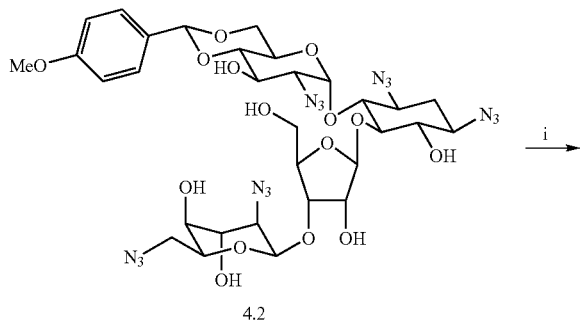

4.2

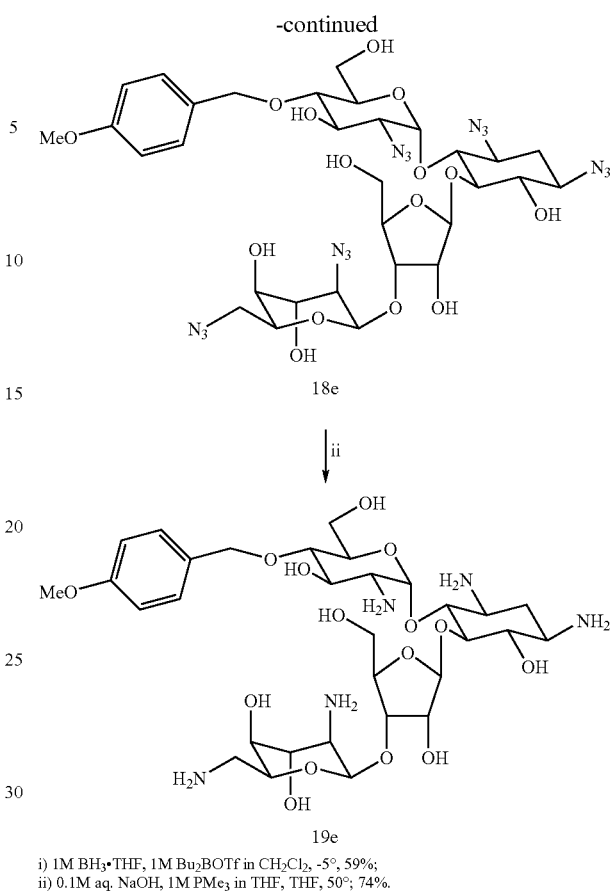

i) 1M BH$_3$·THF, 1M Bu$_2$BOTf in CH$_2$Cl$_2$, -5°, 59%;
ii) 0.1M aq. NaOH, 1M PMe$_3$ in THF, THF, 50°; 74%.

1,3,2',2''',6'''-Pentadeamino-1,3,2',2''',6'''-pentaazido-4'-O-p-methoxybenzylparomomycin (18e)

Under N$_2$, 4.2 (204 mg, 0.236 mmol) cooled to -5° C. was treated with 1M BH$_3$.THF (2.36 ml) and 1M Bu$_2$BOTf in CH$_2$Cl$_2$ (0.236 ml), and stirred at -5° C.-0° C. for 50 min. After completion Et$_3$N (0.1 ml) and MeOH (0.1 ml) were added. Reaction mixture was coevaporated with MeOH three times. FC gave 18e (120 mg, 59%). R$_f$ (AcOEt/CHCl$_3$/MeOH 2:2:0.25) 0.55. White solid, m.p. 65-68° C. [α]$_D^{25}$=+99.3 (c=1.63, MeOH). IR (ATR): 3374m, 2942w, 2874w, 2102s, 1770w, 1631w, 1612w, 1514w, 1453w, 1369w, 1331w, 1248m, 1143w, 1101m, 1075m, 1027s. HR-Maldi-MS: 888.2942 (100, [M+Na]$^+$, C$_{31}$H$_{43}$N$_{15}$NaO$_{15}$$^+$; calc. 888.2961); 456.0339 (91, [M+H]$^{2+}$+Na, C$_{15.5}$H$_{22}$N$_{7.5}$NaO$_{7.5}$$^{2+}$; calc. 456.1468).

4'-p-Methoxybenzylparomomycin (19e)

A soln. of 18e (60 mg, 0.058 mmol) in THF (2 ml) was treated with 0.1M NaOH soln. (0.5 ml) and 1M PMe$_3$ in THF (0.346 ml) and stirred for 4 h at 50° C. After evaporation, FC and coevaporation with 10% AcOH gave 19e as an acetic salt (44 mg, 74%) R$_f$ (MeOH/CHCl$_3$/NH$_{3aq}$. 1:3:2) 0.33. White solid, m.p. 190° C. (dec.). [α]$_D^{25}$=+48.93 (c=0.32, H$_2$O). IR (ATR): 3115m (br), 2874w, 1609w, 1513m, 1405m, 1333w, 1248w, 1050s, 1031s. HR-Maldi-MS: 736.3597 (100, [M+H]$^+$, C$_{31}$H$_{54}$N$_5$O$_{15}$$^+$; calc. 736.3616).

Example: 2

Biological Assay

In the following the biological assay used for determining the activity of the compounds of the invention as exemplified in example 1 above to selectively target bacterial 16S ribosomal RNA and not to target at all or target to a substantially less degree eukaryotic cytosolic and/or mitochiondrial ribosomes is described in detail.

Production of Recombinant *M. smegmatis* Strains

The strain used for introduction/selection of mutational alterations was a genetically modified derivative of *Mycobacterium smegmatis* carrying a single functional chromosomal rRNA operon (Sander et al. Mol. Microbiol. 1996, 22: 841-848). This strain, termed *M. smegmatis* rrn⁻, allowed for the selection of mutational rRNA gene alterations using a plasmid carrying the rRNA gene with the respective mutational alteration.)

The rRNA gene carried on the plasmid encodes either the complete rRNA operon (Prammananan et al. Antimicrob. Agents Chemother. 1999, 43: 447-453) or a non-functional rRNA gene fragment of approximately 1.0 kb (Pfister et al. Antimicrob. Agents Chemother. 2003, 47: 1496-1502). PCR-mutagenesis in vitro was used to generate the mutagenized rRNA gene fragment. In the case of a partial rRNA gene fragment the mutagenized rRNA gene fragment was cloned into vectors pMV261 or pMV361 (Sander et al. Mol. Microbiol. 2002, 46: 1295-1304; Pfister et al. Antimicrob. Agents Chemother. 2003, 47: 1496-1502) to result in vectors carrying a partial rRNA gene fragment of approximately 1.0 kb with the mutational alteration introduced. In the case of plasmids carrying the complete rRNA operon the mutagenized rRNA gene fragment obtained by PCR was cloned into vectors pMV361 rRNA or pMV261 rRNA using appropriate restriction sites (Prammananan et al. Antimicrob. Agents Chemother. 1999, 43: 447-453). Vectors pMV361 rRNA and pMV261 rRNA carried a complete copy of the rRNA operon from *M. smegmatis* (Sander et al. Mol. Microbiol. 1997, 26: 469-480). Introduction of mutations into the plasmid encoded rRNA was confirmed by sequencing.

The single rRNA allelic derivative of *M. smegmatis*, i.e. *M. smegmatis* rrn, was used for transformation of the plasmids. The strain was made electro-competent and transformed according to standard techniques and as described previously (Sander et al. Mol. Microbiol. 1997, 26: 469-484). Following primary selection, the plasmid-encoded mutational rRNA gene alteration was transferred into the single chromosomal rRNA operon by means of RecA-mediated homologous recombination (Prammananan at al. Antimicrob. Agents Chemother. 1999, 43: 447-453). Introduction of the mutational rRNA gene alteration into the single functional chromosomal rRNA operon by gene conversion was confirmed by sequence determination.

In another aspect of the technique, the single functional chromosomal rRNA operon was inactivated and the synthesis of ribosomal RNA was driven exclusively by the mutated plasmid-encoded rRNA operon.

The following demonstrates one way of producing a strain with all endogenous rrn genes deleted and with functional ribosomal RNA produced by a plasmid encoded rRNA operon.

A combination of positive, e.g. aph, and negative-selectable markers, e.g. sacB, was used for unmarked deletion mutagenesis. In brief, the sacB gene was cloned into the mycobacterial expression vector pMV361 (Stover et al. Nature 1991, 351:456-460) to result in pMS32a. In pMS32a, sacB is located downstream of the hsp60 promoter. A restriction fragment of pMS32a carrying the hsp60p-sacB construct was transferred into the cloning vector pGEM-7 (Promega) to result in plasmid pZ130 which was used as backbone in the construction of both rrnA and rrnB replacement vectors. Chromosomal DNA sequences flanking the 5' and 3' region of each rrn operon were obtained by PCR and cloned into pZ130. Following further modifications, the rrn replacement vectors were obtained. As example, the generation of the rrnB replacement vector is described here and the strategy for inactivation of rrnB illustrated in FIG. 1.

For complementation, a functional rrnB operon was cloned into an integration-proficient vector. Following the strategy outlined in FIG. 2 a derivative of *M. smegmatis*, i.e. strain ΔrrnA ΔrrnB attB::prrnB, was obtained where both endogenous chromosomal rRNA operons are inactivated by gene deletion across the entire 16S, 23S, and 5S rRNA genes (rrs, rrl, and rrf, see FIG. 1). This strain is completely devoid of chromosomal rRNA genes and rRNA is exclusively transcribed from plasmid DNA.

Such strains are particularly useful because they avoid the interference of the bacterial cell's own naturally occurring ribosomal activity with that of the introduced at least partially heterologous, mitochondrial or cytosolic bacterial ribosomes in the assay methods of the present invention.

Ribosomal drug susceptibility was studied by determining the minimal inhibitory concentrations, as described in detail in Pfister et al. 2003 and 2005 (see above).

The recombinants carrying the respective mutational alterations in the functional rRNA operon were colony-purified and subjected to determinations of minimal inhibitory concentrations (MIC) to determine ribosomal drug susceptibility. Cultures from single colonies were grown in LB medium supplemented with 0.05% Tween 80 and used for MIC tests in a microtiter plate format. Starting cultures contained 200 μl of bacterial cells at an optical density of 0.025 at 600 nm, and the respective drug was added in twofold series of dilution. The MIC was defined as the drug concentration at which the growth of the cultures was completely inhibited after 72 h of incubation at 37° C., corresponding to 24 generations.

Key nucleotides which distinguish the prokaryotic from the eukaryotic decoding site are 16S rRNA positions 1408 (bacterial ribosome: A, eukaryotic cytosolic ribosomes: G) and 1491 (bacterial ribosomes: G, eukaryotic cytosolic ribosomes: A, eukaryotic mitochondrial ribosome: C).

As demonstrated by the results in table 1 below the compounds of the invention are highly selective for bacterial ribosomal RNA. Hence, they are highly effective in antibiotic therapy of bacterial infection in mammals, in particular humans and they can be dosed higher than current non-selective antibiotics that have to be dosed much lower in order to avoid damage to the mammal's mitochondrial and cytosolic RNA.

TABLE 1

Activity of selected compounds and comparators towards bacterial and mutant ribosomes carrying key nucleotides of the deconding site as determined by investigating minimal inhibitory concentrations (mg/ml)

| | ΔrrnB μg/ml | ΔrrnB 1408G μg/ml | ΔrrnB 1491A μg/ml | ΔrrnB 1491C μg/ml |
| --- | --- | --- | --- | --- |
| Paromomycin | 1 | 64 | 64 | ≥512 |
| Neomycin B | 0.5-1 | >512 | 4 | 16-32 |
| 5.1 | 4 | 512 | 512 | >512 |
| 5.2 | 4 | >512 | >512 | >512 |

TABLE 1-continued

Activity of selected compounds and comparators towards bacterial and mutant ribosomes carrying key nucleotides of the decoding site as determined by investigating minimal inhibitory concentrations (mg/ml)

| | ΔrrnB µg/ml | ΔrrnB 1408G µg/ml | ΔrrnB 1491A µg/ml | ΔrrnB 1491C µg/ml |
|---|---|---|---|---|
| 5.3 | 4-8 | 256-512 | 512 | >512 |
| 5.4 | 8-16 | >512 | >512 | >512 |
| 5.5 | 4-8 | ≥512 | >512 | >512 |
| 5.6 | 4 | 512 | >512 | >512 |
| 5.7 | 2-4 | 256-512 | 256 | >512 |
| 5.8 | 4 | >512 | >512 | >512 |
| 5.9 | 4 | 128-256 | 128-256 | 128 |
| 5.10 | 16-32 | >512 | >512 | >512 |
| 5.11 | 64 | 128 | 64-128 | 64 |
| 5.12 | 2-4 | >512 | >512 | >512 |
| 5.13 | 32 | >512 | >512 | >512 |
| 5.14 | 32-64 | >512 | >512 | >512 |
| 5.15 | 2-4 | 256-512 | 512 | 512 |
| 5.16 | 4-16 | 512 | 512 | >512 |
| 5.17 | 2-4 | >512 | 512 | 512 |
| 5.18 | 2-4 | 256-512 | 256 | >512 |
| 5.19 | 4-8 | 512 | 256-512 | 256 |
| 5.20 | 2-4 | >512 | 512 | 512 |
| 5.21 | 8-16 | >512 | >512 | >512 |
| 5.22 | 8-16 | >512 | >512 | >512 |
| 5.23 | 32 | >512 | >512 | >512 |
| 5.24 | 64 | 256 | 256 | 128-256 |
| 5.25 | 1 | 512 | ≥512 | ≥512 |
| 5.26 | 2-4 | ≥512 | ≥512 | ≥512 |
| 5.27 | 32-64 | >512 | >512 | >512 |
| 5.28 | 4 | 512 | 512 | >512 |
| 5.29 | 4-8 | >512 | >512 | >512 |
| 11 | 4 | >512 | ≥512 | >512 |
| 15 | 32-64 | >512 | >512 | >512 |
| 19a | 2 | ≥512 | ≥512 | >512 |
| 19b | 8 | >512 | >512 | ≥512 |
| 19c | 8-16 | ≥512 | ≥512 | 512 |
| 19d | 16 | >512 | >512 | >512 |
| 19e | 8 | >512 | >512 | >512 |

Example 3

Antibiotic Resistance

Selected compounds of the present invention were tested for antibiotic susceptibility using clinical isolates of *Staphylococci*, *Enterococci* and *Escherichia coli* as well as strains carrying defined resistance determinants and compared to well known antibiotics of the state of the art. Drug susceptibility was determined in standard MIC assays, i.e. by determination of the minimal drug concentration required to inhibit bacterial growth in vitro.

The results indicate:
1. The selected compounds are active against clinical isolates with resistance to standard aminoglycosides
2. The selected compounds are not modified by defined aminoglycoside resistance determinants, e.g. ANT4', AAC6', APH2'', AAC3, ANT2''

The results are summarized in table 2 below, where the numbers correspond to MIC values in µg/ml.

TABLE 2

Minimal inhibitory concentrations (mg/l) of comparator compounds against clinical bacterial isolates and strains with defined resistance determinants

| | | | Gentamicin | Kanamycin A | Tobramycin | Neomycin | Paromomycin |
|---|---|---|---|---|---|---|---|
| AG011 | *Staph. aureus* | clinical isolate | 4 | 16 | 8 | 4 | 8 |
| AG013 | *Staph. epi.* | clinical isolate | ≥256 | ≥256 | ≥256 | 64-128 | ≥256 |
| AG014 | *Staph. epi.* | clinical isolate | ≥256 | ≥256 | 256 | 32 | ≥256 |
| AG016 | *S. aureus* | BM3002 | 1 | 4-8 | 0.5-1 | 1-2 | 2-4 |
| AG015 | *S. aureus* | BM3002 (ANT4') | 4 | 256 | ≥256 | 128 | >256 |
| AG017 | *E. faecalis* | JH2-2 | 8-16 | 32-64 | 16-32 | 64 | 128-256 |
| AG019 | *E. faecalis* | JH2-2 (APH2'' AAC6') | >256 | >256 | >256 | >256 | >256 |
| AG001 | *E. coli* | clinical isolate | 4 | 16 | 4 | | |
| AG002 | *E. coli* | clinical isolate | 2 | 16 | 4 | | |
| AG003 | *E. coli* | clinical isolate | ≥256 | 32 | 32 | | |
| AG004 | *E. coli* | clinical isolate | >256 | 64 | 64 | | |
| AG006 | *E. coli* | BM13 | 4 | 8 | 2 | | |
| AG007 | *E. coli* | BM13 (AAC3) | 128 | 8 | 8 | | |
| AG008 | *E. coli* | BM13 (ANT2'') | 64 | 128 | 64 | | |

TABLE 2-continued

Minimal inhibitory concentrations (mg/l) of comparator compounds against clinical bacterial isolates and strains with defined resistance determinants

| | | | | | |
|---|---|---|---|---|---|
| AG009 | E. coli | BM13 AAC(6')-1B | 32 | >256 | 128-256 |

| | | | 11 | 5.1 | 5.8 | 5.25 | 5.17 |
|---|---|---|---|---|---|---|---|
| AG011 | Staphylococcus aureus | clinical isolate | 8 | 8 | 4-8 | 4 | 4 |
| AG013 | Staphylococcus epidermidis | clinical isolate | 16 | 8-16 | 8 | 4-8 | 4-8 |
| AG014 | Staph. epi. | clinical isolate | 8 | 8 | 8-16 | 4 | 4 |
| AG016 | Staph. aureus | BM3002 | 16-32 | 16-32 | 8 | 8 | 8 |
| AG015 | Staph. aureus | BM3002 (ANT4') | 32 | 32-64 | 16 | 8-16 | 32 |
| AG017 | Enterococcus faecalis | JH2-2 | 32-64 | 32-64 | 16-32 | 8 | 32 |
| AG019 | E. faecalis | JH2-2 (APH2" AAC6') | >256 | 256 | 64 | 32 | 128 |
| AG001 | E. coli | clinical isolate | 64 | 64 | 32 | 32-64 | 32-64 |
| AG002 | E. coli | clinical isolate | 32-64 | 64 | — | 32-64 | 32-64 |
| AG003 | E. coli | clinical isolate | 32-64 | 32 | — | 32 | 32-64 |
| AG004 | E. coli | clinical isolate | 64 | 32-64 | 16-32 | 32 | 32 |
| AG006 | E. coli | BM13 | 32 | 32 | 64 | 16-32 | 32 |
| AG007 | E. coli | BM13 (AAC3) | 32 | 32 | 64 | 16-32 | 32 |
| AG008 | E. coli | BM13 (ANT2") | 64-128 | 32 | 64 | 32 | 32 |
| AG009 | E. coli | BM13 AAC(6')-1B | 64-128 | 128 | 64 | 64-128 | 64-128 |

| | | | 5.26 | 5.20 | 19c | 19a |
|---|---|---|---|---|---|---|
| AG011 | Staphylococcus aureus | clinical isolate | 4 | 1-2 | — | 2 |
| AG013 | Staphylococcus epidermidis. | clinical isolate | 4-8 | 1 | 4-8 | 4 |
| AG014 | Staph. epi | clinical isolate | 4 | 1 | 2 | 2 |
| AG016 | Staph. aureus | BM3002 | 8 | 4 | 4 | 4 |
| AG015 | Staph. aureus | BM3002 (ANT4') | 16-32 | 8-16 | 16 | 8-16 |
| AG017 | Enterococcus faecalis | JH2-2 | 16-32 | 8-16 | 8-16 | 8-16 |
| AG019 | E. faecalis | JH2-2 (APH2" AAC6') | 64-128 | 8-16 | 32 | 32-64 |
| AG001 | E. coli | clinical isolate | 32-64 | 8 | 16-32 | 8-16 |
| AG002 | E. coli | clinical isolate | 64 | — | 16 | 16 |
| AG003 | E. coli | clinical isolate | 32 | — | 8-16 | 8-16 |
| AG004 | E. coli | clinical isolate | 32 | 8 | 16 | 8-16 |
| AG006 | E. coli | BM13 | 32 | 8-16 | 8-16 | 8-16 |
| AG007 | E. coli | BM13 (AAC3) | 32 | 16-32 | 8-16 | 8-16 |
| AG008 | E. coli | BM13 (ANT2") | 32 | 16 | 8-16 | 8-16 |
| AG009 | E. coli | BM13 AAC(6')-1B | 128 | 16-32 | 32 | 32 |

The invention claimed is:

1. A compound of formula (I):

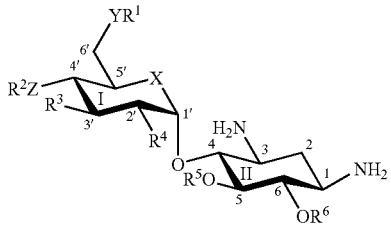

wherein:
X, Y and Z are independently selected from the group consisting of —O—, —NH—, —S—, substituted or unsubstituted —CH$_2$— and a direct bond to R$^1$ and/or R$^2$, with the proviso that X is not NH;

R$^1$ and R$^2$ are independently selected from the group consisting of hydrogen, linear or branched, substituted or non-substituted alkyl, alkenyl, alkynyl, alkylidene, carbocycle and YR$^1$ and ZR$^2$ together form a substituted or non-substituted cycloalkyl or a corresponding heterocyclic ring, with the proviso that R$^2$ is not H;

R$^3$ and R$^4$ are independently selected from the group consisting of hydrogen, amino and hydroxyl;

R$^5$ is a glycosyl selected from the group consisting of monosaccharides and disaccharides; and R$^6$ is hydrogen;

and their diastereoisomers or enantiomers in the form of their bases or salts of physiologically compatible acids.

2. The compound of claim 1, wherein R$^1$ and R$^2$ are independently selected from the group consisting of hydrogen, linear or branched, substituted or non-substituted C$_1$-C$_{12}$ alkyl, C$_2$-C$_{12}$ alkenyl, alkynyl, or alkylidene, C$_3$-C$_{12}$ cycloalkyl, C$_3$-C$_{20}$ aryl, C$_3$-C$_{20}$ heteroaryl and C$_3$-C$_{20}$ heterocyclic, with the proviso that R$^2$ is not H.

3. The compound of claim 2, wherein C$_3$-C$_{20}$ aryl is aralkyl.

4. The compound of claim 1, wherein Y and Z are oxygen.

5. The compound of claim 1, wherein X, Y and Z are oxygen.

6. The compound of claim 1, wherein YR$^1$ is not NH$_2$, and YR$^1$ and ZR$^2$ together form a substituted or non-substituted cycloalkyl or a corresponding heterocyclic ring.

7. The compound of claim 6, wherein YR$^1$ and ZR$^2$ together form a 6-membered 4',6'-cycloalkyl or substituted 4',6'-cycloalkyl ring.

8. The compound of claim 1, wherein R$^1$ is a substituted or non-substituted (C$_1$-C$_5$ alkyl)aryl group and R$^2$ is hydrogen and/or R$^2$ is selected from the group consisting of a linear or branched, substituted or non-substituted C$_1$-C$_7$ alkyl, C$_2$-C$_7$ alkenyl, alkynyl, or alkylidene, C$_3$-C$_7$ cycloalkyl, C$_3$-C$_7$ aryl, C$_3$-C$_7$ heteroaryl and C$_3$-C$_7$ heterocyclic and R$^1$ is hydrogen.

9. The compound of claim 8, wherein C$_3$-C$_7$ aryl is aralkyl.

10. The compound of claim 1, wherein R$^3$ is hydroxyl and/or R$^4$ is amino.

11. The compound of claim 1, wherein R$^5$ is 2,6-diamino-2,6-dideoxy-β-l-idopyranosyl-(1→3)-β-d-ribofuranosyl moiety or a 3-amino-3-deoxy-α-d-glucopyranosyl moiety.

12. The compound of claim 1, according to formula (II):

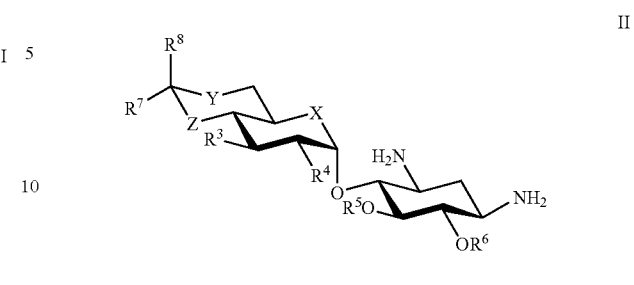

wherein:
X, Y and Z are independently selected from the group consisting of —O—, —NH—, —S—, substituted or non-substituted —CH$_2$—, with the proviso that X is not NH;

R$^7$ is selected from hydrogen, linear or branched, substituted or non-substituted alkyl, alkenyl, alkynyl, alkylidene, and carbocycle;

R$^8$ is selected from the group consisting of hydrogen, OH, NH$_2$, NR$_a$R$_b$, SH, SR$_a$, OR$_a$ and a linear or branched, substituted or non-substituted C$_1$-C$_8$ alkyl, with the proviso that when R$^8$ is OH with the proviso that the compound is stable, and wherein R$_a$ and R$_b$ are each C$_1$-C$_8$ alkyl;

R$^3$ and R$^4$ are independently selected from the group consisting of hydrogen, amino and hydroxyl;

R$^5$ is monosaccharide or disaccharide; and

R$^6$ is hydrogen.

13. The compound of claim 12, wherein X, Y and Z are all oxygen.

14. The compound of claim 12, wherein R$^8$ is C$_1$-C$_4$ alkyl.

15. The compound of claim 12, wherein R$_a$ and R$_b$ are each C$_1$-C$_4$ alkyl.

16. The compound of claim 12, wherein R$^3$ and R$^4$ are each amino or hydroxyl.

17. The compound of claim 12, wherein R$^5$ is 2,6-diamino-2,6-dideoxy-β-l-idopyranosyl-(1→3)-β-d-ribofuranosyl moiety.

18. The compound of claim 12, wherein R$^7$ is selected from hydrogen, a linear or branched, substituted or non-substituted C$_1$-C$_8$ alkyl; a substituted or non-substituted C$_3$-C$_8$ cycloalkyl, C$_5$-C$_{20}$ aryl, and C$_5$-C$_{20}$ heteroaryl; and wherein R$^7$ further comprises a halogen selected from chlorine, bromine, fluorine and iodine.

19. The compound of claim 18, wherein C$_1$-C$_8$ alkyl is substituted linear C$_1$-C$_3$ alkyl.

20. The compound of claim 19, wherein substituted linear C$_1$-C$_3$ alkyl is aryl-substituted C$_1$-C$_3$ alkyl.

21. The compound of claim 20, wherein aryl-substituted C$_1$-C$_3$ alkyl is aryl substituted ethyl group.

22. The compound of claim 18, wherein C$_5$-C$_{20}$ aryl is C$_5$-C$_{12}$ aryl.

23. The compound of claim 18, wherein C$_5$-C$_{20}$ heteroaryl is substituted C$_5$-C$_{12}$ heteroaryl.

24. The compound of claim 23, wherein the substituted C$_5$-C$_{12}$ heteroaryl is (C$_1$-C$_7$ alkyl)aryl group.

25. The compound of claim 18, wherein the halogen is fluorine.

26. The compound of claim 12, wherein R$^8$ is selected from the group consisting of hydrogen, halogen and linear or branched, substituted or non-substituted C$_1$-C$_8$ alkyl.

27. The compound of claim 26, wherein substituted or non-substituted C$_1$-C$_8$ alkyl is C$_1$-C$_4$ alkyl.

28. The compound of claim 26, wherein $R^8$ is hydrogen.

29. The compound of claim 1, wherein $R^1$ and $R^2$ are selected from the group consisting of linear or branched, substituted or non-substituted alkyl or cycloalkyl, and wherein one or more of the carbon atoms are independently replaced with a member of the group consisting of oxygen, sulphur and nitrogen.

30. The compound according to claim 29, selected from the group consisting of:
4',6'-O-benzylideneparomomycin,
4',6'-O-p-methoxybenzylideneparomomycin,
4',6'-O-m-methoxybenzylideneparomomycin tetraacetate,
4',6'-O-o-methoxybenzylideneparomomycin,
4',6'-O-2,5-dimethoxybenzylideneparomomycin,
4',6'-O-p-nitrobenzylideneparomomycin,
4',6'-O-m-nitrobenzylideneparomomycin triacetate,
4',6'-O-p-chlorobenzylideneparomomycin,
4',6'-O-3,5-dichlorobenzylideneparomomycin,
4',6'-O-p-cyanobenzylideneparomomycin,
4',6'-O-p-phenylbenzylideneparomomycin,
4',6'-O-p-fluorobenzylideneparomomycin,
4',6'-O-3,5-dimethoxybenzylideneparomomycin,
4',6'-O-3,4,5-trimethoxybenzylideneparomomycin,
4',6'-O-m-chlorobenzylideneparomomycin,
4',6'-O-o-nitrobenzylideneparomomycin,
4',6'-O-p-trifluoromethylbenzylideneparomomycin,
4',6'-O-p-dimethylaminobenzylideneparomomycin,
4',6'-O-1-naphthylideneparomomycin,
4',6'-O-2-naphthylideneparomomycin,
4',6'-O-2-furanylideneparomomycin,
4',6'-O-2-thiophenylideneparomomycin,
4',6'-O-ethylideneparomomycin,
4',6'-O-(2-phenyl)-ethylideneparomomycin,
4',6'-O-(3-phenyl)-propylideneparomomycin,
4',6'-O-(3-phenyl)-propenylideneparomomycin,
4',6'-O-cyclohexylmethylideneparomomycin,
4'-O-benzylparomomycin,
6'-O-benzylparomomycin,
4'-p-chlorobenzyl paromomycin,
4'-p-(trifluoromethyl)benzylparomomycin,
4'-benzyloxymethylparomomycin and
4'-p-methoxybenzylparomomycin.

31. A pharmaceutical composition, comprising as active substance one or more compounds according to claim 1; wherein said compound is optionally combined with conventional excipients and/or carriers.

32. A method of treating a microbial infection, comprising administering to a patient in need thereof a therapeutically effective amount of a pharmaceutical composition comprising one or more compounds according to claim 1; and wherein the microbial infection is a bacterial infection.

33. The method of claim 32, wherein the bacterial infection is selected from trypanosomiasis and leishmaniasis.

34. A method for preparing a compound according to claim 1, comprising one or more of the following steps:
a) providing a compound according to the formula III:

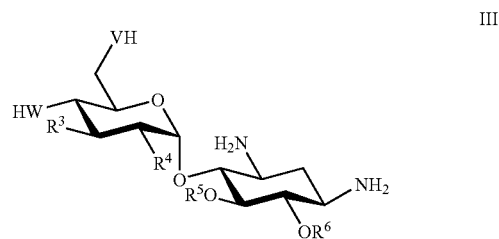

wherein:
V and W are independently selected from —O—, —NH— and —S—;
$R^3$ and $R^4$ are independently selected from hydrogen, amino and hydroxyl;
$R^5$ and $R^6$ are independently selected from hydrogen and glycosyl residues;
b) protecting one or more of the amino groups;
c) optionally protecting one or more of the hydroxy groups;
d1) selectively transforming the optionally protected 4'- and/or 6'-hydroxy groups to $YR^1$ and/or $ZR^2$-groups of formula I or the ring system of formula II; or
d2) selectively deprotecting the protected 4'- and/or 6'-hydroxy groups and selectively transforming the deprotected 4'- and/or 6'-hydroxy groups to $YR^1$ and/or $ZR^2$-groups of formula I or the ring system of formula II;
e) deprotecting the one or more amino groups; and
f) deprotecting the one or more hydroxy groups;
wherein the order of steps b) and c) as well as e) and f) may be reversed.

* * * * *